(12) United States Patent
Nicou et al.

(10) Patent No.: US 11,730,688 B2
(45) Date of Patent: *Aug. 22, 2023

(54) COMPOSITION FOR DYEING THE HAIR, COMPRISING A HETEROCYCLIC OXIDATION BASE AND A 2-AMINO-5-ETHYLPHENOL COUPLER

(71) Applicant: L'OREAL, Paris (FR)

(72) Inventors: Valérie Nicou, Saint-Ouen (FR); Aziz Fadli, Aulnay-sous-bois (FR); Frédéric Le Grand, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/062,282

(22) PCT Filed: Dec. 20, 2016

(86) PCT No.: PCT/EP2016/082011
§ 371 (c)(1),
(2) Date: Jun. 14, 2018

(87) PCT Pub. No.: WO2017/108847
PCT Pub. Date: Jun. 29, 2017

(65) Prior Publication Data
US 2018/0369104 A1    Dec. 27, 2018

(30) Foreign Application Priority Data

Dec. 21, 2015 (FR) .................................... 1562908

(51) Int. Cl.
*A61Q 5/10* (2006.01)
*A61K 8/49* (2006.01)
*A61K 8/41* (2006.01)
*A61K 8/38* (2006.01)

(52) U.S. Cl.
CPC ............... *A61K 8/494* (2013.01); *A61K 8/38* (2013.01); *A61K 8/415* (2013.01); *A61K 8/416* (2013.01); *A61Q 5/10* (2013.01); *A61K 2800/42* (2013.01); *A61K 2800/4324* (2013.01); *A61K 2800/88* (2013.01)

(58) Field of Classification Search
CPC ........ A61Q 5/065; A61K 8/494; A61K 8/416; A61K 8/415; A61K 2800/4322; A61K 2800/88; A61K 2800/43
USPC ........................................................ 8/405
See application file for complete search history.

(56) References Cited

U.S. PATENT DOCUMENTS

| 4,003,699 | A | 1/1977 | Rose et al. |
| 4,137,180 | A | 1/1979 | Naik et al. |
| RE30,199 | E | 1/1980 | Rose et al. |
| 4,840,639 | A | 6/1989 | Husemeyer et al. |
| 4,874,554 | A | 10/1989 | Lange et al. |
| 5,061,289 | A | 10/1991 | Clausen et al. |
| 5,380,340 | A | 1/1995 | Neunhoeffer et al. |
| 5,534,267 | A | 7/1996 | Neunhoeffer et al. |
| 5,663,366 | A | 9/1997 | Neunhoeffer et al. |
| 5,766,576 | A | 6/1998 | Lowe et al. |
| 6,099,592 | A | 8/2000 | Vidal et al. |
| 6,099,593 | A | 8/2000 | Terranova et al. |
| 6,284,003 | B1 | 9/2001 | Rose et al. |
| 6,730,789 | B1 | 5/2004 | Birault et al. |
| 9,125,834 | B2* | 9/2015 | Couroux .............. A61K 8/492 |
| 9,220,671 | B2* | 12/2015 | Ascione .............. A61K 8/492 |
| 9,370,477 | B2* | 6/2016 | Allard .............. C07D 471/04 |
| 2005/0011016 | A1* | 1/2005 | Pasquier .............. A61K 8/415 |
| | | | 8/405 |
| 2005/0166335 | A1 | 8/2005 | Vidal et al. |
| 2007/0067926 | A1* | 3/2007 | Schmitt .............. A61K 8/415 |
| | | | 8/405 |
| 2007/0136959 | A1 | 6/2007 | Fadli |
| 2007/0143935 | A1 | 6/2007 | Fadli et al. |
| 2009/0282622 | A1 | 11/2009 | Dahlgren et al. |
| 2012/0180230 | A1 | 7/2012 | Schmenger et al. |
| 2012/0210519 | A1 | 8/2012 | Lim et al. |
| 2013/0312203 | A1 | 11/2013 | Allard et al. |
| 2015/0139925 | A1 | 5/2015 | Kamikawa et al. |
| 2015/0283053 | A1 | 10/2015 | Odman Schmid et al. |

FOREIGN PATENT DOCUMENTS

| CA | 2615230 | A1 | 4/2008 |
| CN | 101312707 | A | 11/2008 |
| DE | 2359399 | A1 | 6/1975 |
| DE | 3843892 | A1 | 6/1990 |
| DE | 1133957 | A1 | 4/1993 |
| DE | 19543988 | A1 | 5/1997 |
| DE | 202005014897 | U1 | 11/2005 |
| EP | 0007537 | A1 | 2/1980 |
| EP | 0770375 | A1 | 5/1997 |
| EP | 1550656 | A1 | 7/2005 |
| EP | 1792606 | A1 | 6/2007 |
| EP | 1792903 | A1 | 6/2007 |
| FR | 2733749 | A1 | 11/1996 |
| FR | 2750048 | A1 | 12/1997 |
| FR | 2801308 | A1 | 5/2001 |
| FR | 2886136 | A1 | 12/2006 |
| FR | 2893027 | A1 | 5/2007 |
| FR | 2988594 | A1 | 10/2013 |

(Continued)

OTHER PUBLICATIONS

International Search Report for counterpart Application No. PCT/EP2016/082000, dated Mar. 28, 2017.

(Continued)

*Primary Examiner* — Eisa B Elhilo
(74) *Attorney, Agent, or Firm* — The Marbury Law Group, PLLC

(57) ABSTRACT

Composition for dyeing the hair, comprising a heterocyclic oxidation base and a 2-amino-5-ethylphenol coupler The present invention relates to a composition for dyeing keratin fibres, comprising a particular heterocyclic oxidation base and a 2-amino-5-ethylphenol coupler. The invention also relates to a process for dyeing keratin fibres using this composition. Finally, the invention relates to the use of such a composition for dyeing keratin fibres, and in particular the hair.

20 Claims, No Drawings

(56) References Cited

FOREIGN PATENT DOCUMENTS

| | | |
|---|---|---|
| GB | 1026978 A | 4/1966 |
| GB | 1153196 A | 5/1969 |
| JP | 02-019576 A | 1/1990 |
| JP | 05-163124 A | 6/1993 |
| JP | 2015-512367 A | 4/2015 |
| WO | 80/00214 A1 | 2/1980 |
| WO | 94/08969 A1 | 4/1994 |
| WO | 94/08970 A1 | 4/1994 |
| WO | 96/15765 A1 | 5/1996 |
| WO | 0135917 A1 | 5/2001 |
| WO | 2004/041225 A1 | 5/2004 |
| WO | 2007/034410 A1 | 3/2007 |
| WO | WO 2010/133640 A2 * 11/2010 ............... A61K 8/41 |
| WO | 2012080289 A2 | 6/2012 |
| WO | 2013/152956 A1 | 10/2013 |
| WO | 2017/108840 A1 | 6/2017 |
| WO | 2017/108841 A1 | 6/2017 |

OTHER PUBLICATIONS

International Search Report for counterpart Application No. PCT/EP2016/082001, dated Mar. 28, 2017.
Porter, M.R., "Handbook of Surfactants," published by Blackie & Son (Glasgow and London), 1991, pp. 116-178.
Todd, Charles, et al., "Volatile Silicone Fluids for Cosmetic Formulations," Cosmetics and Toiletries, vol. 91, Jan. 1976, pp. 29-32.
International Search Report for Application No. PCT/EP2016/082011, dated May 15, 2017.
Notice of Reasons for Refusal for counterpart JP Application No. 2018-532092, dated May 7, 2019 with Translation.
Notice of Reasons for Refusal for counterpart JP Application No. 2018-532093, dated Jul. 1, 2019 with Translation.
Notice of Reasons for Refusal for counterpart JP Application No. 2018-532094, dated May 7, 2019 with Translation.
Translated Chinese Office Action for counterpart Application No. 201680074386.8, dated Jun. 28, 2020.
Translation of Chinese Office Action for counterpart Application No. 201680074381.5 dated Aug. 10, 2020.
Translation of Chinese Office Action for counterpart Application No. 201680074384.9, dated Jul. 24, 2020.
Non-Final Office Action for copending U.S. Appl. No. 16/063,719, dated Sep. 18, 2020.
Translation of Japanese Office Action for counterpart Application No. 2019-145549, dated Oct. 19, 2020.
Final Office Action for copending U.S. Appl. No. 16/063,719, dated Mar. 1, 2021.
Non-Final Office Action for copending U.S. Appl. No. 16/062,207, dated Jul. 7, 2021.

* cited by examiner

COMPOSITION FOR DYEING THE HAIR, COMPRISING A HETEROCYCLIC OXIDATION BASE AND A 2-AMINO-5-ETHYLPHENOL COUPLER

CROSS REFERENCE TO RELATED APPLICATIONS

This is a national stage application of PCT/EP2016/082011, filed internationally on Dec. 20, 2016, which claims priority to French Application No. 1562908, filed on Dec. 21, 2015, both of which are incorporated by reference herein in their entireties.

The present invention relates to a composition for dyeing keratin fibres, comprising a particular heterocyclic oxidation base and a 2-amino-5-ethylphenol coupler.

The invention also relates to a process for dyeing keratin fibres using this composition.

Finally, the invention relates to the use of such a composition for dyeing keratin fibres, and in particular the hair.

Many people have sought for a long time to modify the colour of their hair and in particular to mask their grey hair.

It is known practice to dye keratin fibres, in particular human keratin fibres such as the hair, to obtain "permanent" colourations with dye compositions containing oxidation dye precursors, which are generally known as oxidation bases, such as ortho- or para-phenylenediamines, ortho- or para-aminophenols, or heterocyclic compounds such as pyrazoles, pyrazolinones or pyrazolo-pyridines. These oxidation bases are colourless or weakly coloured compounds which, when combined with oxidizing products, may give rise to coloured compounds via a process of oxidative condensation.

It is also possible to vary the shades obtained with these oxidation bases by combining them with couplers or colour modifiers. The variety of molecules used as oxidation bases and couplers allows a wide range of colours to be obtained.

However, the use of these dye compositions may have a certain number of drawbacks.

Specifically, after application to keratin fibres, the dyeing power obtained may not be entirely satisfactory, or may even be weak, and lead to a restricted range of colours.

The colourations may also not be sufficiently persistent with respect to external agents such as light, shampoo or perspiration, and may also be too selective, i.e. the difference in colouration is too great along the same keratin fibre that is differently sensitized between its end and its root.

It is already known practice to use oxidation bases derived from 3-aminopyrazolo[1,5-a]pyridine in the field of dyeing keratin fibres, in particular the oxidation bases of formulae (I) and (II) below. In particular, such bases are disclosed in documents EP 1 792 903 and EP 1 792 606.

It is also known practice to use oxidation bases of the diamino-N,N-dihydropyrazolone type in the field of dyeing keratin fibres, in particular the hair. In particular, such a base is described in document EP 1 550 656.

By way of example, the 2-amino-5-ethylphenol coupler is known from document DE202005014897. In said document, it is combined with another m-aminophenol coupler and oxidation bases for dyeing the hair in a varied manner. According to said document, it is possible, with such a combination, to obtain uniform colourations from the root to the end of the hair. Said document does not envisage the combination of the 2-amino-5-ethylphenol coupler with oxidation bases of pyrazolopyridine type.

These combinations do not however make it possible to obtain an entirely satisfactory colouration. This is because they do not make it possible to provide good coverage of the keratin fibres, and in particular of depigmented keratin fibres, such as grey hair. Moreover, their dyeing capacity often proves to be limited.

Thus, there is a real need to provide a composition for dyeing keratin fibres, in particular human keratin fibres such as the hair, which does not have the drawbacks mentioned above, i.e. which is capable of leading to a strong colouration with good coverage of grey hair while the same time having good fastness.

These aims and others are achieved by the present invention, one subject of which is thus a composition for dyeing keratin fibres, comprising:
(a) at least one 2-amino-5-ethylphenol coupler, or an addition salt or solvate thereof, and
(b) at least one pyrazole heterocyclic oxidation base chosen from
A1) the pyrazolopyridines of formula (I), and also the addition salts thereof, solvates thereof or solvates of the salts thereof:

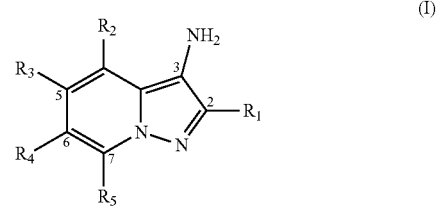

in which:
$R_1$, $R_2$, $R_3$, $R_4$ and $R_5$, which may be identical or different, represent a hydrogen or halogen atom; a radical —NHSO$_3$H; a hydroxyl radical; a radical ($C_1$-$C_4$)alkyl; a radical ($C_1$-$C_4$)alkoxy; a radical ($C_1$-$C_4$)alkylthio; mono($C_1$-$C_4$)alkylamino; a radical di($C_1$-$C_4$)alkylamino in which the two alkyl groups may form, together with the nitrogen atom to which they are attached, a ring that may be interrupted with one or more nitrogen, oxygen or sulfur atoms; a heterocycle; a nitro radical; a phenyl radical; a carbonyl radical; a ($C_1$-$C_4$)alkoxycarbonyl radical; a carboxamido radical; a cyano radical; an amino radical; a sulfonyl radical; a radical —CO$_2$H, a radical —SO$_3$H; a radical —PO$_3$H$_2$; a radical —PO$_4$H$_2$; or a group:

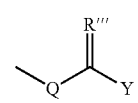

in which R''' represents an oxygen or nitrogen atom, Q represents an oxygen atom, a group NH or NH($C_1$-$C_4$)alkyl, and Y represents a hydroxyl, amino, $C_1$-C4 alkyl, ($C_1$-$C_4$) alkoxy, ($C_1$-$C_4$)alkylamino or di($C_1$-$C_4$)alkylamino radical;
A2) the pyrazolopyridine oxidation bases of formula (II),

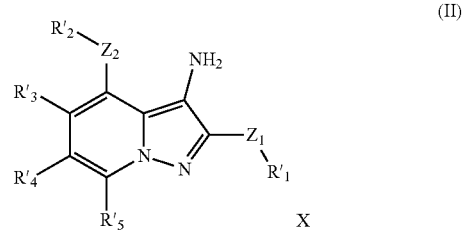

in which:

$Z_1$ and $Z_2$ independently represent:
- a covalent single bond;
- a divalent radical chosen from:
  - a radical $-O(CH_2)_p-$, p denoting an integer ranging from 0 to 6;
  - a radical $-NR'_6(CH_2)_q(C_6H_4)_t-$, q denoting an integer ranging from 0 to 6 and t denoting 0 or 1, $R'_6$ representing a hydrogen atom or a $C_1$-$C_6$ alkyl radical optionally substituted with one or more hydroxyl groups;

$Z_1$ may also represent a divalent radical $-S-$, $-SO-$ or $-SO_2-$ when $R'_1$ is a methyl radical;

$R'_1$ and $R'_2$ independently represent:
- a hydrogen;
- a $C_1$-$C_{10}$ alkyl radical, which is optionally substituted and optionally interrupted with a heteroatom or a group chosen from O, N, Si, S, SO and $SO_2$;
- a halogen;
- a radical $SO_3H$;
- a substituted or unsubstituted, saturated, unsaturated or aromatic, 5- to 8-membered ring, optionally containing one or more heteroatoms or groups chosen from N, O, S, $SO_2$ and $-CO-$, it being possible for the ring to be cationic and/or substituted with a cationic radical;
- a group $-N^+R_{17}R_{18}R_{19}$, $R_{17}$, $R_{18}$ and $R_{19}$ being linear or branched $C_1$-$C_5$ alkyls optionally substituted with one or more hydroxyl groups;

when $Z_1$, respectively $Z_2$, represents a covalent bond, then $R'_1$, respectively $R'_2$, may also represent:
- an optionally substituted $C_1$-$C_6$ alkylcarbonyl radical;
- a radical $-O-CO-R$, $-CO-O-R$, $NR-CO-R'$ or $-CO-NRR'$ in which R and R' independently represent a hydrogen atom or an optionally substituted $C_1$-$C_6$ alkyl radical;

$R'_3$, $R'_4$ and $R'_5$, which may be identical or different, represent:
- a hydrogen atom;
- a hydroxyl radical;
- a $C_1$-$C_6$ alkoxy radical;
- a $C_1$-$C_6$ alkylthio radical;
- an amino radical;
- a monoalkylamino radical;
- a $C_1$-$C_6$ dialkylamino radical in which the alkyl radicals may form, with the nitrogen to which they are attached, a saturated or unsaturated, aromatic or nonaromatic, 5- to 8-membered heterocycle, which may contain one or more heteroatoms or groups chosen from N, O, S, $SO_2$ and CO, it being possible for the heterocycle to be cationic and/or substituted with a cationic radical;
- an optionally substituted $C_1$-$C_6$ alkylcarbonyl radical;
- a radical $-O-CO-R$, $-CO-O-R$, $NR-CO-R'$ or $-CO-NRR'$ with R and R' as defined previously;
- a halogen;
- a radical $-NHSO_3H$;
- an optionally substituted $C_1$-$C_4$ alkyl radical;
- a saturated, unsaturated or aromatic, optionally substituted carbon-based ring;

$R'_3$, $R'_4$ and $R'_5$ may form in pairs a partially saturated or unsaturated ring;

X represents an ion or group of ions making it possible to ensure the electronegativity of the derivative of formula (II); with the proviso that at least one of the groups $R'_1$ and $R'_2$ represents a cationic radical; and A3) the diamino-N,N-dihydropyrazolone derivatives of formula (III), and also the addition salts thereof, solvates thereof or solvates of the salts thereof:

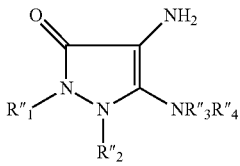

(III)

in which:

$R''_3$ and $R''_4$, which may be identical or different, represent:
- a hydrogen atom;
- a linear or branched $C_1$-$C_6$ alkyl radical optionally substituted with one or more radicals chosen from the group constituted of a radical $OR''_5$, a radical $NR''_6R''_7$, a carboxyl radical, a sulfonic radical, a carboxamido radical $CONR''_6R''_7$, a sulfonamido radical $SO_2NR''_6R''_7$, a heteroaryl, an aryl optionally substituted with one or more $(C_1$-$C_4)$alkyl, hydroxyl, $C_1$-$C_2$ alkoxy, amino or (di)alkyl $(C_1$-$C_2)$amino groups;
- an aryl radical optionally substituted with one or more $(C_1$-$C_4)$alkyl, hydroxyl, $C_1$-$C_2$ alkoxy, amino or (di)alkyl $(C_1$-$C_2)$amino;
- a 5- or 6-membered heteroaryl radical, optionally substituted with one or more radicals chosen from $(C_1$-$C_4)$alkyl and $(C_1$-$C_2)$alkoxy;

$R''_3$ and $R''_4$ may also form, together with the nitrogen atom to which they are attached, a 5- or 7-membered heterocycle, the carbon atoms of which may be replaced with an optionally substituted oxygen or nitrogen atom;

$R''_5$, $R''_6$ and $R''_7$, which may be identical or different, represent:
- a hydrogen atom;
- a linear or branched $C_1$-$C_4$ alkyl radical optionally substituted with one or more radicals chosen from hydroxyl, $C_1$-$C_2$ alkoxy, carboxamido $CONR''_8R''_9$, sulfonyl $SO_2R''_8$, aryl optionally substituted with a $(C_1$-$C_4)$alkyl, hydroxyl, $C_1$-$C_2$ alkoxy, amino or (di)alkyl$(C_1$-$C_2)$amino; aryl optionally substituted with a $(C_1$-$C_4)$alkyl, hydroxyl, $C_1$-$C_2$ alkoxy, amino or (di)alkyl$(C_1$-$C_2)$amino;

$R''_6$ and $R''_7$, which may be identical or different, may also represent a carboxamido radical $CONR''_8R''_9$; a sulfonyl radical $SO_2R''_8$;

$R''_8$ and $R''_9$, which may be identical or different, represent a hydrogen atom; a linear or branched $C_1$-$C_4$ alkyl radical optionally substituted with one or more hydroxyl or $C_1$-$C_2$ alkoxy;

$R''_1$ and $R''_2$ form, together with the nitrogen atom(s) to which they are attached, a saturated or unsaturated 5- to 7-membered heterocycle optionally substituted with one or more radicals chosen from the group constituted of halogen atoms and amino, (di)alkyl$(C_1$-$C_4)$amino, hydroxyl, carboxyl, carboxamido and $(C_1$-$C_2)$alkoxy radicals, $C_1$-$C_4$ alkyl radicals optionally substituted with one or more hydroxyl, amino, (di)alkylamino, alkoxy, carboxyl or sulfonyl radicals.

Another subject of the present invention is a process the dyeing keratin fibres in which the composition according to the invention is applied to said fibres.

The invention also relates to the use of said composition for dyeing keratin fibres, and in particular the hair.

This composition gives particularly good coverage of depigmented keratin fibres such as grey hair.

The composition according to the invention makes it possible to produce particularly intense, chromatic and sparingly selective colourations, i.e. colourations that are uniform along the length of the fibre.

Moreover, the colourations obtained by means of the composition according to the invention withstand the various attacking factors to which the hair may be subjected, such as light, bad weather, washing and perspiration.

Other subjects, characteristics, aspects and advantages of the invention will emerge even more clearly on reading the description and the examples that follow.

In that which follows and unless otherwise indicated, the limits of a range of values are included within this range, in particular in the expressions "of between" and "ranging from . . . to . . . ".

In the context of the present invention, the expression "at least one" is equivalent to the expression "one or more".

The present invention also covers the mesomeric forms and the stereoisomers of the various oxidation dyes of use for the invention.

It should be noted that, in the text hereinbelow, unless otherwise indicated, the limits of a range of values are included in that range.

In the context of the invention, and unless indicated otherwise, the term "alkyl" used for the alkyl radicals and also for the groups comprising an alkyl part means a linear or branched carbon-based chain comprising from 1 to 4 carbon atoms, which is unsubstituted or substituted with one or more heterocycles, or with one or more phenyl groups or with one or more groups chosen from halogen atoms such as chlorine, bromine, iodine and fluorine; hydroxyl, alkoxy, amino, carbonyl, carboxamido, sulfonyl, —$CO_2H$, —$SO_3H$, —$PO_3H_2$, —$PO_4H_2$, —$NHSO_3H$, sulfonamide, mono($C_1$-$C_4$)alkylamino or tri($C_1$-$C_4$)alkylammonium radicals, or alternatively with a di($C_1$-$C_4$)alkylamino radical in which the two alkyl groups may form, together with the nitrogen atom of said di($C_1$-$C_4$)alkylamino group to which they are attached, a ring that may be interrupted with one or more nitrogen, oxygen or sulfur atoms.

Similarly, according to the invention, the term "alkoxy" used for the alkoxy radicals and also for the groups comprising an alkoxy part means a linear or branched O-carbon-based chain comprising from 1 to 4 carbon atoms, which is unsubstituted or substituted with one or more groups chosen from heterocycles; halogen atoms such as chlorine, bromine, iodine and fluorine; hydroxyl, amino, carbonyl, carboxamido, sulfonyl, —$CO_2H$, —$SO_3H$, —$PO_3H_2$, —$PO_4H_2$, —$NHSO_3H$, sulfonamide, mono($C_1$-$C_4$)alkylamino or tri($C_1$-$C_4$)alkylammonium radicals, or alternatively with a di($C_1$-$C_4$)alkylamino radical in which the two alkyl groups may form, together with the nitrogen atom of said di($C_1$-$C_4$)alkylamino group to which they are attached, a ring that may be interrupted with one or more nitrogen, oxygen or sulfur atoms.

According to the invention, the term "heterocycle" is intended to mean an aromatic or non-aromatic 5-, 6-, 7- or 8-membered ring containing from 1 to 3 heteroatoms chosen from nitrogen, sulfur and oxygen atoms. These heterocycles may be fused to other heterocycles or to a phenyl group. They may be substituted with a halogen atom; a ($C_1$-$C_4$) alkyl radical; a ($C_1$-$C_4$)alkoxy radical; a hydroxyl radical; an amino radical; a ($C_1$-$C_4$)alkylamino radical; a di($C_1$-$C_4$) alkylamino radical in which the two alkyl groups may form, together with the nitrogen atom to which they are attached, a ring that may be interrupted with one or more nitrogen, oxygen or sulfur atoms. These heterocycles may also be quaternized with a ($C_1$-$C_4$)alkyl radical.

(a) The 2-amino-5-ethylphenol Coupler

The composition according to the invention comprises one or more 2-amino-5-ethylphenol couplers, in free form, or addition salts thereof or solvates thereof.

The addition salts are in particular chosen from addition salts with an acid, such as hydrochlorides, hydrobromides, sulfates, citrates, succinates, tartrates, lactates, tosylates, benzenesulfonates, methanesulfonates, phosphates and acetates, and the addition salts with a base such as sodium hydroxide, potassium hydroxide, ammonia, amines or alkanolamines.

Moreover, the solvates more particularly represent the hydrates of the 2-amino-5-ethylphenol coupler and/or the combination of the 2-amino-5-ethylphenol coupler with a linear or branched $C_1$ to $C_4$ alcohol such as methanol, ethanol, isopropanol or n-propanol. Preferably, the solvates are hydrates.

The total amount of the 2-amino-5-ethylphenol coupler or an addition salt or solvate thereof, present in the composition according to the invention, can range from 0.0001% to 20% by weight, preferably from 0.005% to 10% by weight, and more preferentially from 0.01% to 6% by weight, relative to the total weight of the composition.

(b) Heterocyclic Oxidation Bases

The oxidation bases A1, A2 and A3 can be in hydrate, solvate or salt form.

These oxidation bases may be optionally salified with strong mineral acids, for instance HCl, HBr, HI, $H_2SO_4$ or $H_3PO_4$, or organic acids, for instance acetic acid, lactic acid, tartaric acid, citric acid, succinic acid, benzenesulfonic acid, para-toluenesulfonic acid, formic acid or methanesulfonic acid.

If they contain anionic groups such as —$CO_2H$, —$SO_3H$, —$PO_3H_2$ or —$PO_4H_2$ groups, the compounds of formula (I) may be salified with alkali metal or alkaline-earth metal hydroxides such as sodium hydroxide or potassium hydroxide, with aqueous ammonia or with organic amines.

They may also be in the form of solvates, for example a hydrate or a solvate of a linear or branched alcohol such as ethanol or isopropanol.

Among the oxidation bases A1 of formula (I) above, preference is given to the 3-aminopyrazolo[1,5-a]pyridines corresponding to formula (I') below, and also the addition salts thereof, solvates thereof or solvates of the salts thereof:

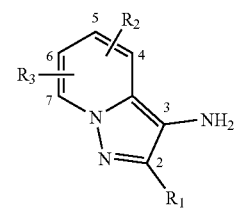

(I')

in which:

$R_1$, $R_2$ and $R_3$, which may be identical or different, represent a hydrogen or halogen atom; a hydroxyl radical; a ($C_1$-$C_4$) alkyl radical; a ($C_1$-$C_4$)alkylthio radical; a ($C_1$-$C_4$)alkoxy radical; an —$NHSO_3H$ radical; an amino radical; a ($C_1$-$C_4$) alkylamino radical; a di($C_1$-$C_4$)alkylamino radical in which the two alkyl groups may form, together with the nitrogen atom to which they are attached, a ring that may be interrupted with one or more nitrogen, oxygen or sulfur atoms; a heterocycle as defined previously; a sulfonamide radical, a carbonyl radical, a (C$_1$-C$_4$)alkoxycarbonyl radical, a carboxamido radical, or a group of formula:

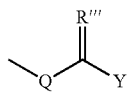

in which R''' represents an oxygen or nitrogen atom, Q represents an oxygen atom, a group NH or NH(C$_1$-C$_4$)alkyl, and Y represents a hydroxyl, amino, C$_1$-C4 alkyl, (C$_1$-C$_4$) alkoxy, (C$_1$-C$_4$)alkylamino or di(C$_1$-C$_4$)alkylamino radical.

Among the 3-aminopyrazolo[1,5-a]pyridines of formula (I), which may be used as oxidation base in the dye compositions in accordance with the invention, mention may be made in particular of:
pyrazolo[1,5-a]pyridin-3-ylamine;
2-acetylaminopyrazolo[1,5-a]pyridin-3-ylamine;
2-morpholin-4-ylpyrazolo[1,5-a]pyridin-3-ylamine;
3-aminopyrazolo[1,5-a]pyridine-2-carboxylic acid;
2-methoxypyrazolo[1,5-a]pyridin-3-ylamino;
(3-aminopyrazolo[1,5-a]pyridin-7-yl)methanol;
2-(3-aminopyrazolo[1,5-a]pyridin-5-yl)ethanol;
2-(3-aminopyrazolo[1,5-a]pyridin-7-yl)ethanol;
(3-aminopyrazolo[1,5-a]pyridin-2-yl)methanol;
3,6-diaminopyrazolo[1,5-a]pyridine;
3,4-diaminopyrazolo[1,5-a]pyridine;
pyrazolo[1,5-a]pyridine-3,7-diamine;
7-morpholin-4-ylpyrazolo[1,5-a]pyridin-3-ylamine;
pyrazolo[1,5-a]pyridine-3,5-diamine;
5-morpholin-4-ylpyrazolo[1,5-a]pyridin-3-ylamine;
2-[(3-aminopyrazolo[1,5-a]pyridin-5-yl)(2-hydroxyethyl) amino]ethanol;
2-[(3-aminopyrazolo[1,5-a]pyridin-7-yl)(2-hydroxyethyl) amino]ethanol;
3-aminopyrazolo[1,5-a]pyridin-5-ol;
3-aminopyrazolo[1,5-a]pyridin-4-ol;
3-aminopyrazolo[1,5-a]pyridin-6-ol;
3-aminopyrazolo[1,5-a]pyridin-7-ol;
2-methoxy-6,7-dimethylpyrazolo[1,5-a]pyridin-3-amine;
2-[(3-aminopyrazolo[1,5-a]pyridin-2-yl)oxy]ethanol;
4-ethyl-2-methoxy-7-methylpyrazolo[1,5-a]pyridin-3-amine hydrochloride;
1-(3-aminopyrazolo[1,5-a]pyridin-2-yl)pyrrolidin-3-ol;
2,2'-[(3-aminopyrazolo[1,5-a]pyridin-2-yl)imino]diethanol;
2-[(3-aminopyrazolo[1,5-a]pyridin-2-yl)amino]ethanol;
N2-(2-pyridin-3-ylethyl)pyrazolo[1,5-a]pyridine-2,3-diamine;
and the addition salts thereof, solvates thereof or solvates of the salts thereof.

Among the bases described above, 2-[(3-aminopyrazolo [1,5-a]pyridin-2-yl)oxy]ethanol, and the addition salts thereof, solvates thereof or solvates of the salts thereof, are particularly preferred.

For the vast majority, the 3-aminopyrazolo[1,5-a]pyridines of formula (I) are compounds that are known in the pharmaceutical field, and are described in particular in patent U.S. Pat. No. 5,457,200. These compounds may be prepared according to synthetic methods that are well known in the literature and as described, for example, in patent U.S. Pat. No. 5,457,200.

The term "cationic ring or heterocycle" is intended to mean a ring containing one or more quaternary ammonium groups.

Examples of radicals of the type —N$^+$R$_{17}$R$_{18}$R$_{19}$ that may be mentioned include trimethylammonium, triethylammonium, dimethylethylammonium, diethylmethylammonium, diisopropylmethylammonium, diethylpropylammonium, β-hydroxyethyldiethylammonium, bis(β-hydroxyethyl) methylammonium and tris(β-hydroxyethyl)ammonium radicals.

Examples of cationic heterocycles include imidazolium, pyridinium, piperazinium, pyrrolidinium, morpholinium, pyrimidinium, thiazolium, benzimidazolium, benzothiazolium, oxazolium, benzotriazolium, pyrazolium, triazolium and benzoxazolium heterocycles.

Examples of cationic heterocycles that may be mentioned include imidazoliums, pyridiniums, piperaziniums, pyrrolidiniums, morpholiniums, pyrimidiniums, thiazoliums, benzimidazoliums, benzothiazoliums, oxazoliums, benzotriazoliums, pyrazoliums, triazoliums and benzoxazoliums.

As examples of derivatives of formula (II), mention may be made of the following compounds in which X$^-$ is as defined previously:

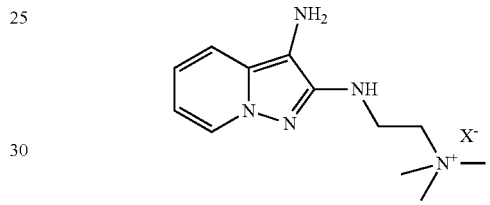

[2-(3-Aminopyrazolo[1,5-a]pyridin-2-ylamino)ethyl]trimethylammonium salt

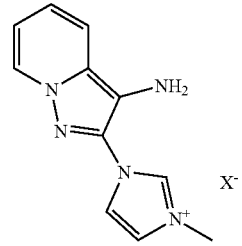

3-(3-Aminopyrazolo[1,5-a]pyridin-2-yl)-1-methyl-3H-imidazol-1-ium salt

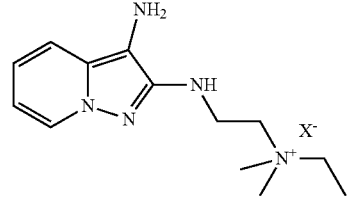

[2-(3-Aminopyrazolo[1,5-a]pyridin-2-ylamino)ethyl]ethyldimethylammonium salt

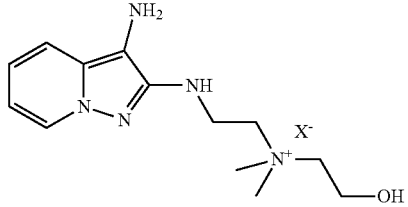

[2-(3-Aminopyrazolo[1,5-a]pyridin-2-ylamino)ethyl]-(2-hydroxyethyl)dimethylammonium salt

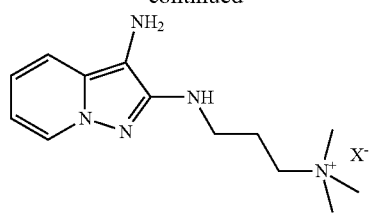

[3-(3-Aminopyrazolo[1,5-a]pyridin-2-ylamino)propyl]trimethylammonium salt

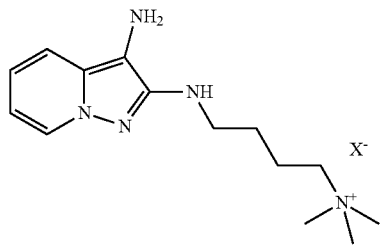

[4-(3-Aminopyrazolo[1,5-a]pyridin-2-ylamino)butyl]trimethylammonium salt

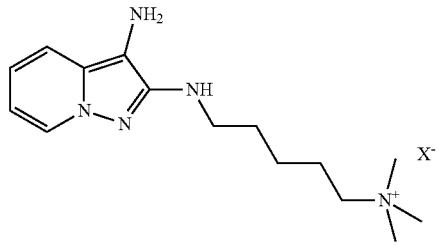

[5-(3-Aminopyrazolo[1,5-a]pyridin-2-ylamino)pentyl]trimethylammonium salt

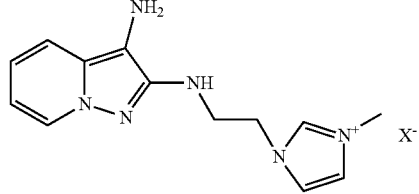

3-[2-(3-Aminopyrazolo[1,5-a]pyridin-2-ylamino)ethyl]-1-methyl-3H-imidazol-1-ium salt

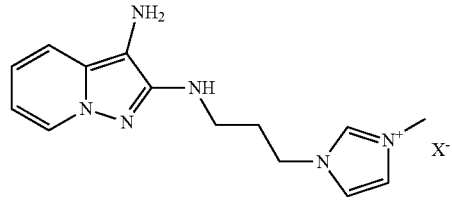

3-[3-(3-Aminopyrazolo[1,5-a]pyridin-2-ylamino)propyl]-1-methyl-3H-imidazol-1-ium salt

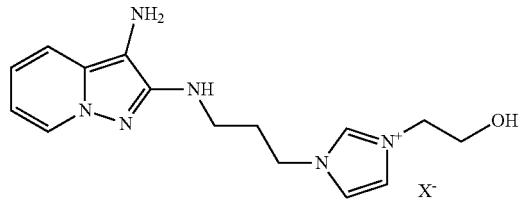

3-[3-(3-Aminopyrazolo[1,5-a]pyridin-2-ylamino)propyl]-1-(2-hydroxyethyl)-3H-imidazol-1-ium salt

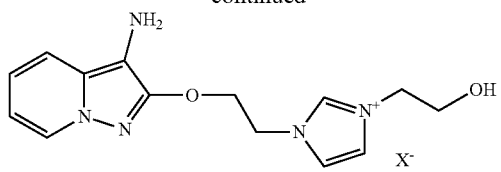

3-[2-(3-Aminopyrazolo[1,5-a]pyridin-2-yloxy)ethyl]-1-(2-hydroxyethyl)-3H-imidazol-1-ium salt

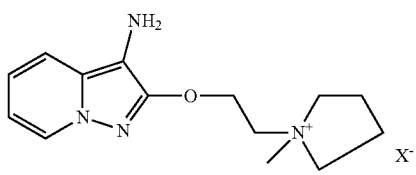

1-{2-[(3-Aminopyrazolo[1,5-a]pyridin-2-yl)oxy]ethyl}-1-methylpyrrolidinium salt

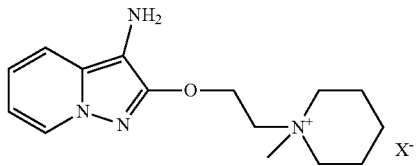

1-{2-[(3-Aminopyrazolo[1,5-a]pyridin-2-yl)oxy]ethyl}-1-methylpiperidinium salt

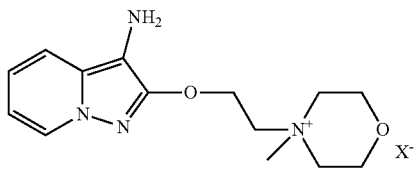

4-{2-[(3-Aminopyrazolo[1,5-a]pyridin-2-yl)oxy]ethyl}-4-methylmorpholin-4-ium salt

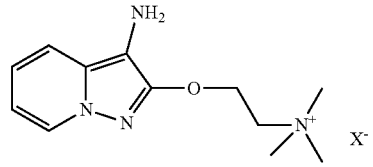

{2-[(3-Aminopyrazolo[1,5-a]pyridin-2-yl)oxy]ethyl}trimethylammonium salt

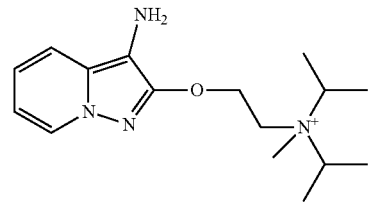

{2-[(3-Aminopyrazolo[1,5-a]pyridin-2-yl)oxy]ethyl}diisopropylmethylammonium salt

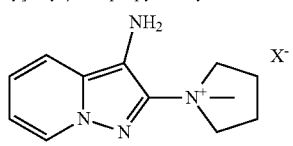

1-(3-Aminopyrazolo[1,5-a]pyridin-2-yl)-1-methylpyrrolidinium salt

-continued

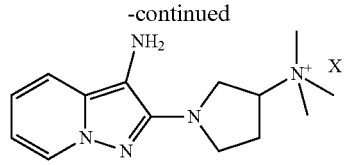

[1-(3-Aminopyrazolo[1,5-a]pyridin-2-
yl)pyrrolidin-3-yl]trimethylammonium salt

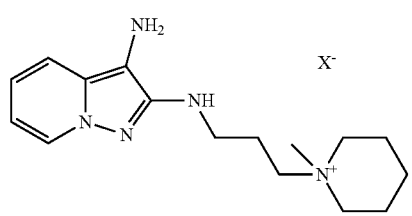

1-[3-(3-Aminopyrazolo[1,5-a]pyridin-2-
ylamino)propyl]-1-methylpiperidinium salt

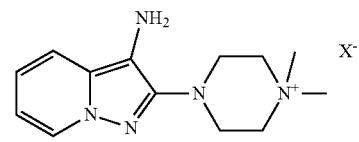

4-(3-Aminopyrazolo[1,5-a]pyridin-2-yl)-1,1-
dimethylpiperazin-1-ium salt

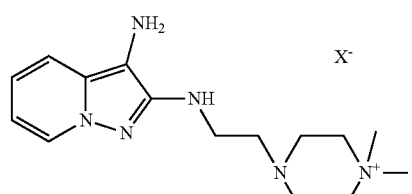

4-[2-(3-Aminopyrazolo[1,5-a]pyridin-2-
ylamino)ethyl]-1,1-dimethylpiperazin-1-ium salt

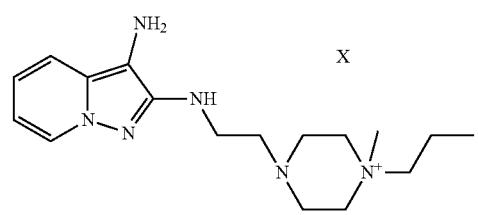

4-[2-(3-Aminopyrazolo[1,5-a]pyridin-2-
ylamino)ethyl]-1-methyl-1-propylpiperazin-1-ium salt

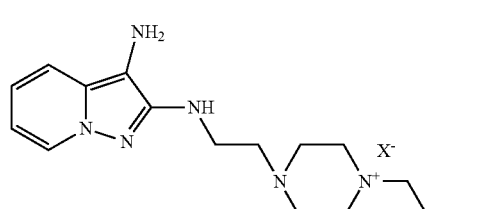

4-(3-Aminopyrazolo[1,5-a]pyridin-2-yl)-1-
(2-hydroxyethyl)piperazin-1-ium salt

-continued

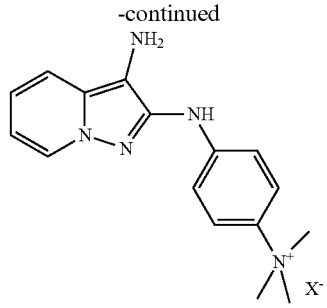

[4-(3-Aminopyrazolo[1,5-a]pyridin-2-
ylamino)phenyl]trimethylammonium salt

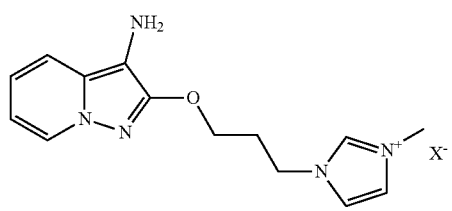

3-[3-(3-Aminopyrazolo[1,5-a]pyridin-2-
yloxy)propyl]-1-methyl-3H-imidazol-1-ium salt

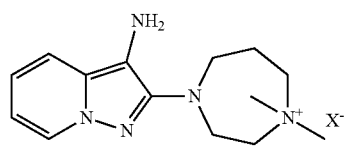

4-(3-Aminopyrazolo[1,5-a]pyridin-2-yl)-
1,1-dimethyl-[1,4]diazepan-1-ium salt

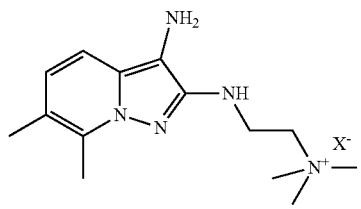

[2-(3-Amino-6,7-dimethylpyrazolo[1,5-a]pyridin-
2-ylamino)ethyl]trimethylammonium salt

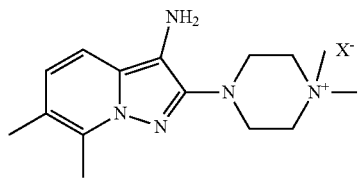

4-(3-Amino-6,7-dimethylpyrazolo[1,5-a]
pyridin-2-yl)-1,1-dimethyl-piperazin-1-ium salt

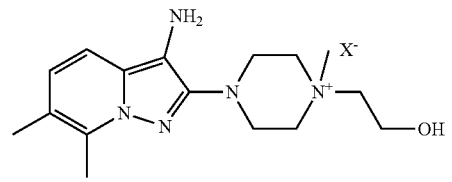

4-(3-Amino-6,7-dimethylpyrazolo[1,5-a]
pyridin-2-yl)-1-(2-hydroxyethyl)-1-methylpiperazin-1-ium salt -continued

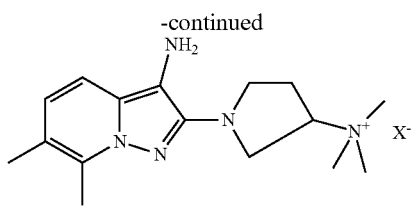

[1-(3-Amino-6,7-dimethylpyrazolo[1,5-a]
pyridin-2-yl)pyrrolidin-3-yl]-trimethylammonium salt

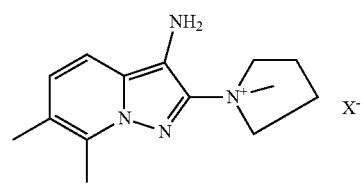

1-(3-Amino-6,7-dimethylpyrazolo[1,5-a]
pyridin-2-yl)-1-methylpyrrolidinium salt

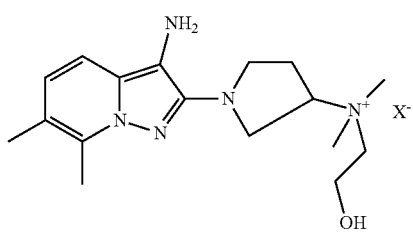

[1-(3-Amino-6,7-dimethylpyrazolo[1,5-a]
pyridin-2-yl)pyrrolidin-3-yl]-(2-hydroxyethyl)
dimethylammonium salt

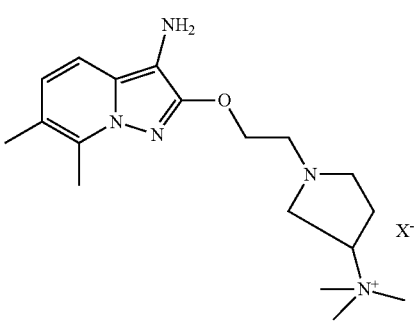

{1-[2-(3-Amino-6,7-dimethylpyrazolo[1,5-a]
pyridin-2-yloxy)ethyl]pyrrolidin-3-
yl}trimethylammonium salt

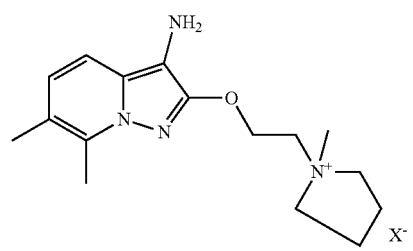

1-{2-[(3-Amino-6,7-dimethylpyrazolo[1,5-a]
pyridin-2-yl)oxy)ethyl]-1-methylpyrrolidinium salt

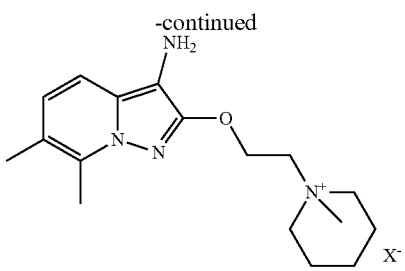

1-{2-[(3-Amino-6,7-dimethylpyrazolo[1,5-a]
pyridin-2-yl)oxy]ethyl}-1-methylpiperidinium salt

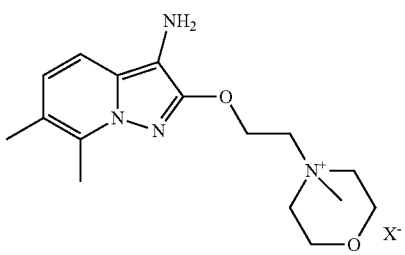

4-{2-[(3-Amino-6,7-dimethylpyrazolo[1,5-a]
pyridin-2-yl)oxy]ethyl}-4-methylmorpholin-4-ium salt

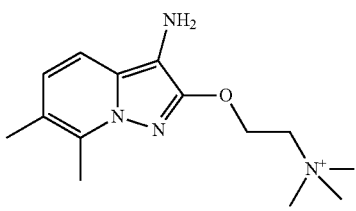

{2-[(3-Amino-6,7-dimethylpyrazolo[1,5-a]
pyridin-2-yl)oxy]ethyl}trimethylammonium salt

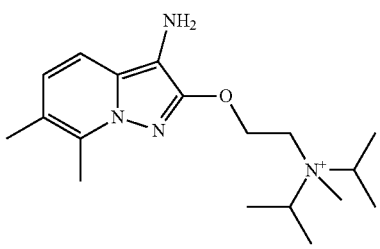

{2-[(3-Amino-6,7-dimethylpyrazolo[1,5-a]pyridin-2-
yl)oxy]ethyl}diisopropylmethylammonium salt

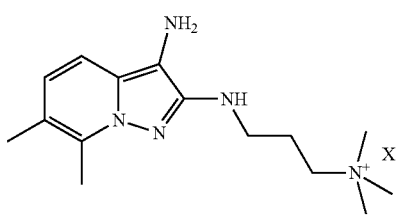

[3-(3-Amino-6,7-dimethylpyrazolo[1,5-a]pyridin-2-
ylamino)propyl]trimethyl-ammonium -continued

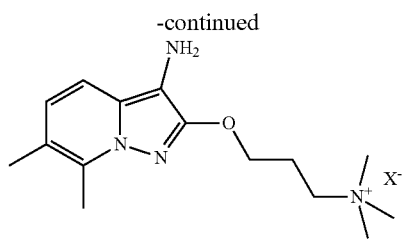

[3-(3-Amino-6,7-dimethylpyrazolo[1,5-a]pyridin-2-yloxy)propyl]trimethylammonium

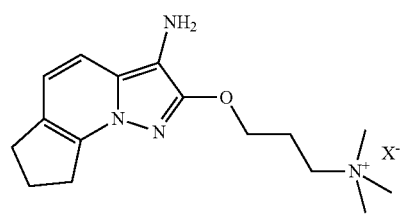

[3-(3-Amino-7,8-dihydro-6H-cyclopenta[e]pyrazolo[1,5-a]pyridin-2-yloxy)propyl]trimethylammonium salt

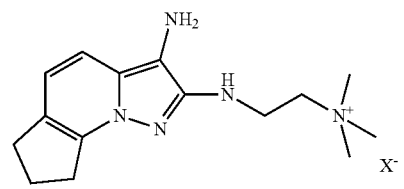

{2-[(3-Amino-7,8-dihydro-6H-cyclopenta[e]pyrazolo[1,5-a]pyridin-2-yl)amino]ethyl}trimethylammonium salt

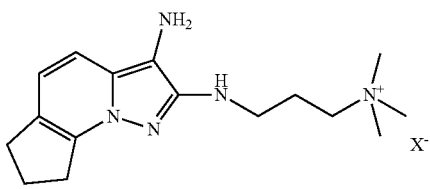

{3-[(3-Amino-7,8-dihydro-6H-cyclopenta[e]pyrazolo[1,5-a]pyridin-2-yl)amino]propyl}trimethylammonium salt

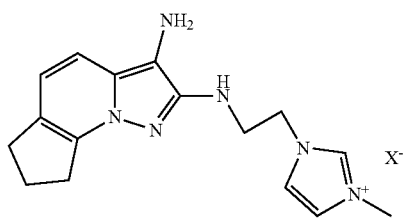

1-{2-[(3-Amino-7,8-dihydro-6H-cyclopenta[e]pyrazolo[1,5-a]pyridin-2-yl)amino]ethyl}-3-methyl-1H-imidazol-3-ium salt

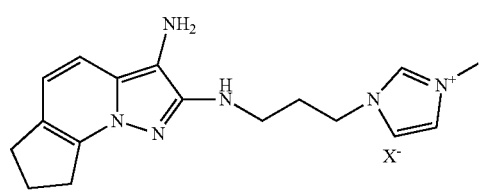

1-{3-[(3-Amino-7,8-dihydro-6H-cyclopenta[e]pyrazolo[1,5-a]pyridin-2-yl)amino]propyl}-3-methyl-1H-imidazol-3-ium salt -continued

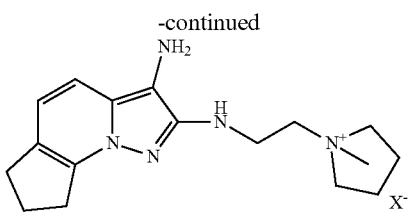

1-{2-[(3-Amino-7,8-dihydro-6H-cyclopenta[e]pyrazolo[1,5-a]pyridin-2-yl)amino]ethyl}-1-methylpyrrolidinium salt

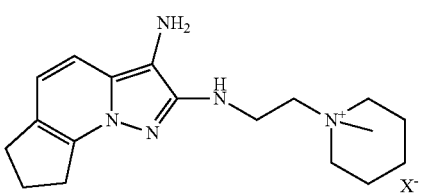

1-{2-[(3-Amino-7,8-dihydro-6H-cyclopenta[e]pyrazolo[1,5-a]pyridin-2-yl)amino]ethyl}-1-methylpiperidinium salt

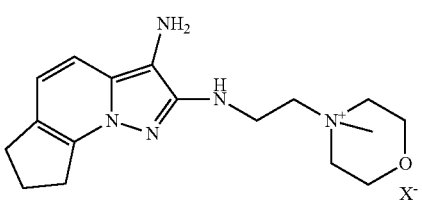

4-{2-[(3-Amino-7,8-dihydro-6H-cyclopenta[e]pyrazolo[1,5-a]pyridin-2-yl)amino]ethyl}-4-methylmorpholin-4-ium salt

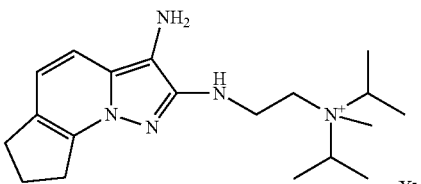

{2-[(3-Amino-7,8-dihydro-6H-cyclopenta[e]pyrazolo[1,5-a]pyridin-2-yl)amino]ethyl}diisopropylmethylammonium salt

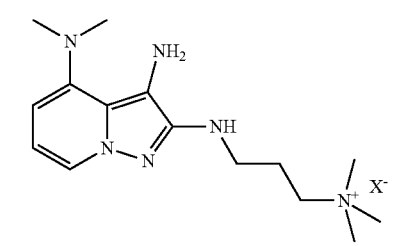

[3-(3-Amino-4-dimethylaminopyrazolo[1,5-a]pyridin-2-ylamino)propyl]trimethylammonium salt

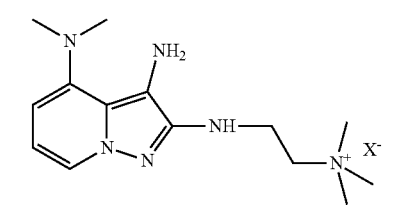

[2-(3-Amino-4-dimethylaminopyrazolo[1,5-a]pyridin-2-ylamino)ethyl]trimethylammonium salt

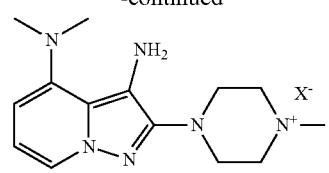

4-(3-Amino-4-dimethylaminopyrazolo[1,5-a]
pyridin-2-yl)-1-methylpiperazin-1-ium salt

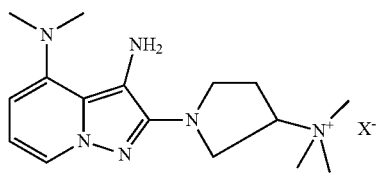

[1-(3-Amino-4-dimethylaminopyrazolo[1,5-a]
pyridin-2-yl)pyrrolidin-3-yl]trimethylammonium salt

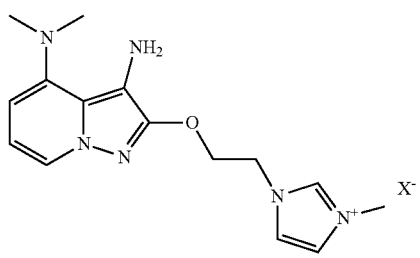

3-[2-(3-Amino-4-dimethylaminopyrazolo[1,5-a]
pyridin-2-yloxy)ethyl]-1-methyl-3H-imidazol-1-ium salt

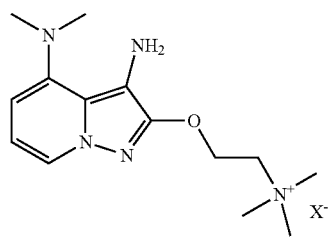

[2-(3-Amino-4-dimethylaminopyrazolo[1,5-a]
pyridin-2-yloxy)ethyl]trimethylammonium salt

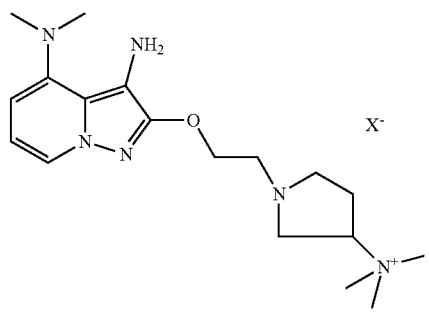

{1-[2-(3-Amino-4-dimethylaminopyrazolo[1,5-a]
pyridin-2-yloxy)ethyl]pyrrolidin-3-yl}
trimethylammonium salt

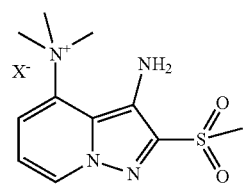

(3-Amino-2-methanesulfonylpyrazolo[1,5-a]
pyridin-4-yl)trimethylammonium salt

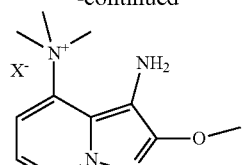

(3-Amino-2-methoxypyrazolo[1,5-a]
pyridin-4-yl)trimethylammonium salt

When $R'_1$ or $R'_2$ denotes a heterocycle, this heterocycle is preferably a cationic heterocycle or a heterocycle substituted with a cationic radical. By way of example, mention may be made of imidazoles substituted with a quaternary ammonium radical or imidazoliums, piperazines substituted with a quaternary ammonium radical or piperaziniums, pyrrolidines substituted with a quaternary ammonium radical or pyrrolidiniums, and diazepanes substituted with a quaternary ammonium radical or diazepaniums.

According to a different embodiment, $R'_1$ or $R'_2$ represents a group $-N^+R_{17}R_{18}R_{19}$, $R_{17}$, $R_{18}$ and $R_{19}$ being linear or branched $C_1$-$C_5$ alkyls optionally substituted with one or more hydroxyl groups, such as trialkylammonium, tri(hydroxyalkyl)ammonium, hydroxyalkyldialkylammonium or di(hydroxyalkyl)alkylammonium.

The radicals $R'_3$, $R'_4$ and $R'_5$, independently, may be a hydrogen atom or an optionally substituted $C_1$-$C_4$ alkyl radical. By way of example, mention may be made of methyl, ethyl, hydroxyethyl, aminoethyl, propyl and butyl radicals. According to one particular embodiment, $R'_3$, $R'_4$ and $R'_5$ independently represent a hydrogen atom or a $C_1$-$C_4$ alkyl radical.

According to one particular embodiment, $R'_4$ and $R'_5$ together form a partially saturated or unsaturated 5- or 8-membered ring, in particular a cyclopentene or cyclohexene, which is optionally substituted.

According to one particular embodiment, the compound of formula (II) corresponds to formula (II') below:

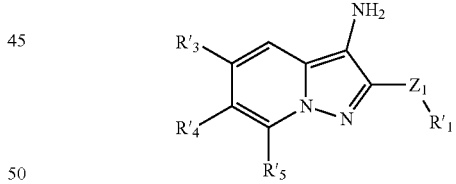

(II')

In which $Z_1$, $R'_1$, $R'_3$, $R'_4$ and $R'_5$ are as defined previously.

According to one particular embodiment of this formula, $Z_1$ represents a covalent bond, a radical $-NR'_6(CH_2)_q-$ or a radical $-O(CH_2)_p-$ and $R'_1$ is a cationic radical.

As cationic oxidation bases of formula (II), the following bases are most particularly preferred:

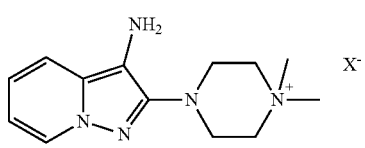

4-(3-Aminopyrazolo[1,5-a]pyridin-2-yl)-1,1-dimethylpiperazin-1-ium salt

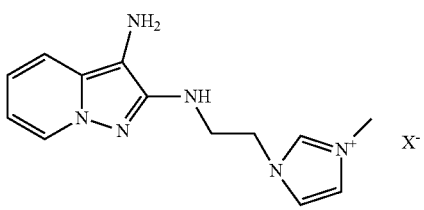

3-[2-(3-Aminopyrazolo[1,5-a]pyridin-2-ylamino)ethyl]-1-methyl-3H-imidazol-1-ium salt and the addition salts thereof, solvates thereof or solvates of the salts thereof.

For the oxidation bases A3 of formula (III), the radicals $R''_1$ and $R''_2$ form, together with the nitrogen atoms to which are attached, a saturated or unsaturated 5- or 6-membered ring, which is optionally substituted.

Preferably, the radicals $R''_1$ and $R''_2$ form, together with the nitrogen atoms to which they are attached, a pyrazolidine or pyridazolidine ring, optionally substituted with one or more $C_1$-$C_4$ alkyl, hydroxyl, $(C_1$-$C_2)$alkoxy, carboxyl, carboxamido, amino or $(di)(C_1$-$C_2)$alkylamino radicals.

Even more advantageously, the radicals $R''_1$ and $R''_2$ form, together with the nitrogen atoms to which they are attached, a pyrazolidine or pyridazolidine ring.

As regards the radicals $R''_3$ and $R''_4$, these radicals, which may be identical or different, are more particularly chosen from a hydrogen atom; a linear or branched $C_1$-$C_6$ and preferably $C_1$-$C_4$ alkyl radical, optionally substituted with one or more hydroxyl, $(C_1$-$C_2)$alkoxy, amino or $(di)(C_1$-$C_2)$alkylamino; a phenyl radical optionally substituted with one or more hydroxyl, amino or $(C_1$-$C_2)$alkoxy radicals.

Preferably, the radicals $R''_3$ and $R''_4$, which may be identical or different, are chosen from a hydrogen atom and methyl, ethyl, isopropyl, 2-hydroxyethyl, 3-hydroxypropyl, 2-hydroxypropyl and 2-carboxyethyl radicals. According to one particular embodiment, the radicals $R''_3$ and $R''_4$ represent a hydrogen atom.

According to another embodiment, the radicals $R''_3$ and $R''_4$ form, together with the nitrogen atom to which they are attached, a 5- or 7-membered ring chosen from pyrrolidine, piperidine, homopiperidine, piperazine and homopiperazine heterocycles; said rings possibly being substituted with one or more hydroxyl, amino, $(di)(C_1$-$C_2)$alkylamino, carboxyl, carboxamido or $C_1$-$C_4$ alkyl radicals optionally substituted with one or more hydroxyl, amino or $C_1$-$C_2$ (di)alkylamino radicals.

More particularly, the radicals $R''_3$ and $R''_4$ form, together with the nitrogen atom to which they are attached, a 5- or 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(2-hydroxyethyl)aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine and N-(2-hydroxyethyl)homopiperazine.

Preferably, the radicals $R''_3$ and $R''_4$ form, together with the nitrogen atom to which they are attached, a 5- or 7-membered ring chosen from pyrrolidine, 3-hydroxypyrrolidine, 3-aminopyrrolidine, 3-dimethylaminopyrrolidine, pyrrolidine-2-carboxylic acid, 3-hydroxypyrrolidine-2-carboxylic acid, piperidine, hydroxypiperidine, homopiperidine, diazepane, N-methylhomopiperazine and N-β-hydroxyethylhomopiperazine, in particular the radicals $R''_3$ and $R''_4$ form, together with the nitrogen atom to which they are attached, a five-membered ring such as pyrrolidine, 3-hydroxypyrrolidine, 3-aminopyrrolidine or 3-dimethylaminopyrrolidine.

As examples of oxidation bases of formula (III), mention may be made of the compounds below, or the addition salts thereof, solvates thereof or solvates of the salts thereof:

2,3-diamino-6,7-dihydro-1H,5H-pyrazolo[1,2-a]pyrazol-1-one;
2-amino-3-methylamino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(2-hydroxyethyl)amino-6,7-dihydro-1H,5H-pyrazolo[1,2-a]pyrazol-1-one;
2-amino-3-(2-hydroxypropyl)amino-6,7-dihydro-1H,5H-pyrazolo[1,2-a]pyrazol-1-one;
2-amino-3-bis(2-hydroxyethyl)amino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
2-amino-3-(3-hydroxypyrrolidin-1-yl)-6,7-dihydro-1H,5H-pyrazolo[1,2-a]pyrazol-1-one;
2-amino-3-(piperidin-1-yl)-6,7-dihydro-1H,5H-pyrazolo[1,2-a]pyrazol-1-one;
2,3-diamino-6-hydroxy-6,7-dihydro-1H,5H-pyrazolo[1,2-a]pyrazol-1-one;
2,3-diamino-6-methyl-6,7-dihydro-1H,5H-pyrazolo[1,2-a]pyrazol-1-one;
2,3-diamino-6-dimethyl-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
2,3-diamino-5,8-dihydro-1H,6H-pyridazino[1,2-a]pyrazol-1-one;
2,3-diamino-6-hydroxy-6,7-dihydro-5H-pyrazolo[1,2-a]pyrazol-1-one;

some of which are featured below to illustrate the names via chemical structures:

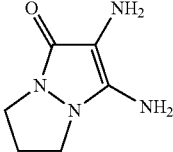 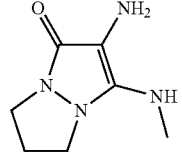

2,3-diamino-6,7-dihydro-1H,5H-pyrazolo[1,2-a]pyrazol-1-one 2-amino,3-aminomethyl-6,7-dihydro-1H,5H-pyrazolo[1,2-a]pyrazol-1-one -continued

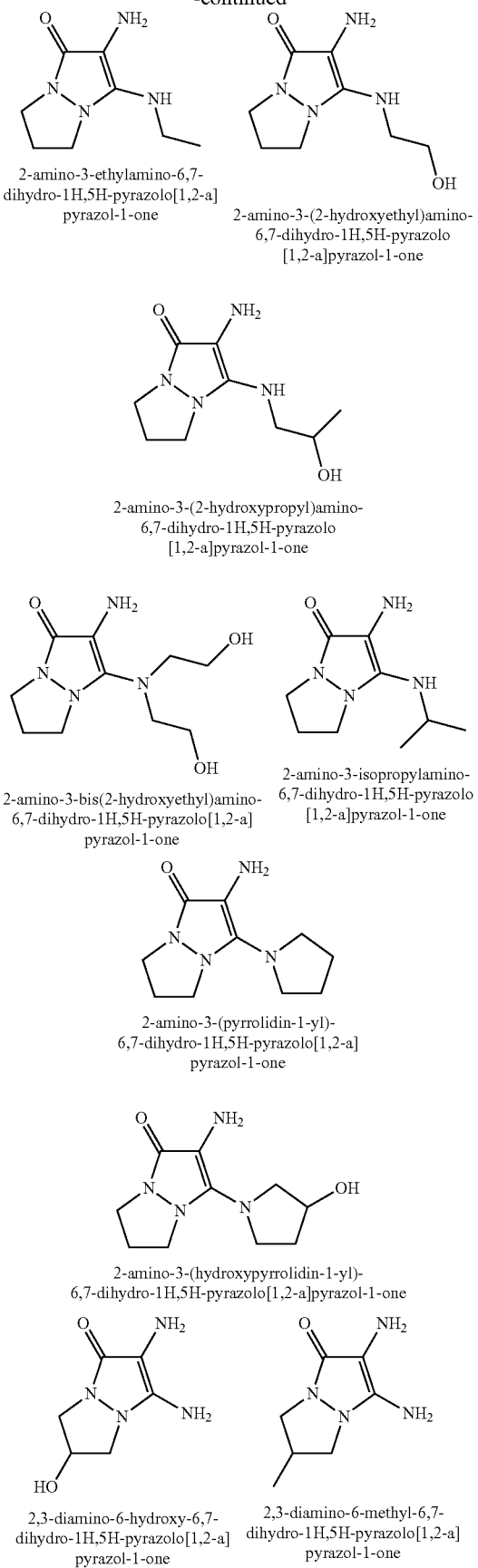

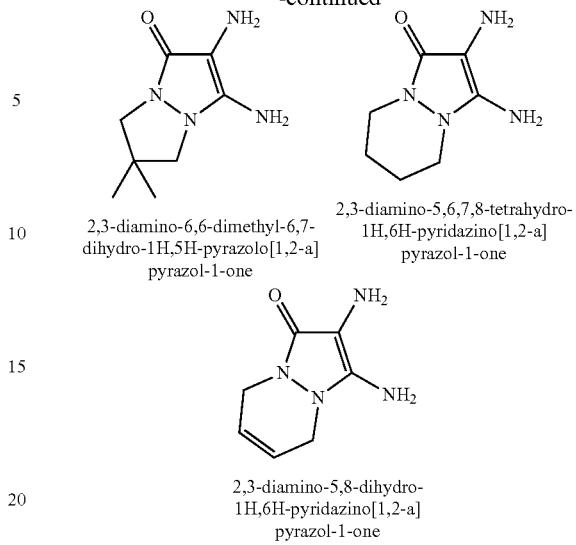

Among these compounds, the diamino-N,N-dihydropyrazolone derivatives of formula (III) or the addition salts thereof, solvates thereof and solvates of the salts thereof are particularly:
2,3-diamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
2-amino-3-(2-hydroxyethyl)amino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
2,3-diamino-6-hydroxy-6,7-dihydro-1H,5H-pyrazolo[1,2-a]pyrazol-1-one.
Preferably, the following oxidation bases:
2,3-diamino-6-hydroxy-6,7-dihydro-1H,5H-pyrazolo[1,2-a]pyrazol-1-one;
2,3-diamino-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
and the addition salts thereof, or solvates thereof or solvates of the salts thereof.

Additional Couplers and Bases

The composition of the invention may contain other additional couplers and oxidation bases Among these couplers other than the 2-amino-5-ethylphenol of use for the invention, mention may in particular be made of meta-phenylenediamines, meta-aminophenols other than 2-amino-5-ethylphenol, meta-diphenols, naphthalene couplers, heterocyclic couplers, the addition salts thereof, solvates thereof and mixtures thereof.

Among the couplers that can be used in the composition according to the invention, mention may particularly be made of 6-hydroxybenzomorpholine, 1,3-dihydroxybenzene, 2-methyl-1,3-dihydroxybenzene, 1-hydroxy-3-aminobenzene, 2-methyl-5-hydroxyethylaminophenol, 2,4-diaminophenoxyethanol, 4-amino-2-hydroxytoluene, 2,4- dichloro-3-aminophenol, 5-amino-4-chloro-o-cresol, 5-amino-6-chloro-o-cresol, 4-chloro-1,3-dihydroxybenzene, 1-β-hydroxyethyloxy-2,4-diaminobenzene, 2-amino 4-(β-hydroxyethylamino)-1-methoxybenzene, 1,3-bis(2,4-diaminophenoxy) propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 1,5-dihydroxynaphthalene, 2,7-naphthalenediol, 1-acetoxy-2-methylnaphthalene, 6-hydroxyindole, 4-hydroxyindole, 4-hydroxy N-methylindole, 2-amino-3-hydroxypyridine, 3,5-diamino-2,6-dimethoxypyridine, 2,6-dihydroxy-3-4-dimethylpyridine, 3-amino-2-methylamino-6-methoxypyridine, 6-hydroxybenzomorpholine, 1-N-(β-hydroxyethyl)amino-3,4-methylenedioxybenzene, 2,6-bis(β-hydroxyethylamino)toluene, 3-methyl-1-phenyl 5-pyrazolone, the addition salts thereof with an acid and the solvates thereof.

Preferably, the additional coupler(s) present in the composition according to the invention are chosen from 6-hydroxybenzomorpholine, 2,4-diaminophenoxyethanol, 1,3-dihydroxybenzene, 1-hydroxy-3-aminobenzene, 2-methyl-5-hydroxyethylaminophenol, 2-methyl-1,3-dihydroxybenzene, 2-amino 3-hydroxypyridine, the addition salts thereof, solvates thereof and mixtures thereof. The total amount of coupler(s) present in the composition according to the invention can range from 0.0001% to 20% by weight, preferably from 0.005% to 10% by weight and more preferentially from 0.01% to 6% by weight relative to the total weight of the composition.

Among the additional oxidation bases, mention may be made of para-phenylenediamines, bis(phenyl)alkylenediamines, para-aminophenols, bis-para-aminophenols, ortho-aminophenols and heterocyclic bases other than those described previously, and the addition salts thereof and solvates thereof.

Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-γ-hydroxypropyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid and solvates thereof.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,6-dioxaoctane and the addition salts thereof with an acid and solvates thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol and 4-amino-2-fluorophenol, and the addition salts thereof with an acid and solvates thereof.

Among the ortho-aminophenols, examples that may be mentioned include 2-aminophenol, 2-amino-5-methylphenol, 2-amino-6-methylphenol and 5-acetamido-2-aminophenol, and the addition salts thereof with an acid and solvates thereof.

Among the pyridine derivatives, mention may be made of the compounds described, for example, in patents GB 1 026 978 and GB 1 153 196, such as 2,5-diaminopyridine, 2-(4-methoxyphenyl)amino-3-aminopyridine, 3,4-diaminopyridine, and addition salts thereof with an acid and solvates thereof.

Among the pyrimidine derivatives, mention may be made of the compounds described, for example, in patents DE 2 359 399; JP 88-169 571; JP 05-63124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048, and among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl) amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5-N7,N7-tetramethylpyrazolo[1,5-a]pyrimidine-3,7-diamine and 3-amino-5-methyl-7-imidazolylpropylaminopyrazolo[1,5-a]pyrimidine, and the addition salts thereof and solvates thereof.

Among the pyrazole derivatives, mention may be made of diaminopyrazole bases, in particular the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3- hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, 4-5-diamino-1-(β-methoxyethyl)pyrazole, and the addition salts thereof and solvates thereof.

The total amount of oxidation base(s) present in the composition according to the invention can range from 0.0001% to 20% by weight, preferably from 0.005% to 10% by weight and more preferentially from 0.01% to 6% by weight relative to the total weight of the composition.

Surfactants

The composition according to the invention may optionally also comprise one or more surfactants.

The surfactant(s) that may be used in the composition according to the invention may be chosen from non-ionic, cationic, anionic and amphoteric or zwitterionic surfactants.

The composition according to the invention may comprise one or more non-ionic surfactants.

The non-ionic surfactants that may be used are described, for example, in the *Handbook of Surfactants* by M. R. Porter, published by Blackie & Son (Glasgow and London), 1991, pp. 116-178.

Examples of non-ionic surfactants that may be mentioned include the following non-ionic surfactants:

oxyalkylenated ($C_8$-$C_{24}$)alkylphenols;
saturated or unsaturated, linear or branched, oxyalkylenated or glycerolated $C_8$-$C_{40}$ alcohols, comprising one or two fatty chains;
saturated or unsaturated, linear or branched, oxyalkylenated $C_8$ to $C_{30}$ fatty acid amides;
esters of saturated or unsaturated, linear or branched, $C_8$ to $C_{30}$ acids and of polyethylene glycols;
preferably oxyethylenated esters of saturated or unsaturated, linear or branched, $C_8$ to $C_{30}$ acids and of sorbitol;
esters of fatty acids and of sucrose;
($C_8$-$C_{30}$)alkyl(poly)glucosides and ($C_8$-$C_{30}$)alkenyl(poly)glucosides, which are optionally oxyalkylenated (0 to 10 oxyalkylene units) and comprising from 1 to 15 glucose units, ($C_8$-$C_{30}$)alkyl(poly)glucoside esters;
saturated or unsaturated oxyethylenated vegetable oils;
condensates of ethylene oxide and/or of propylene oxide;
N—($C_8$-$C_{30}$)alkylglucamine and N—($C_8$-$C_{30}$)acylmethylglucamine derivatives;
aldobionamides;
amine oxides;
oxyethylenated and/or oxypropylenated silicones;
and mixtures thereof.

The oxyalkylene units are more particularly oxyethylene or oxypropylene units, or their combination, preferably oxyethylene units.

The number of moles of ethylene oxide and/or propylene oxide preferably ranges from 1 to 250, more particularly from 2 to 100 and better still from 2 to 50; the number of moles of glycerol ranges in particular from 1 to 50 and better still from 1 to 10.

Advantageously, the non-ionic surfactants according to the invention do not comprise any oxypropylene units.

By way of example of glycerolated non-ionic surfactants, use may preferably be made of monoglycerolated or polyglycerolated $C_8$ to $C_{40}$ alcohols comprising from 1 to 50 mol of glycerol, preferably from 1 to 10 mol of glycerol.

As examples of compounds of this type, mention may be made of lauryl alcohol containing 4 mol of glycerol (INCI name: Polyglyceryl-4 Lauryl Ether), lauryl alcohol comprising 1.5 mol of glycerol, oleyl alcohol comprising 4 mol of glycerol (INCI name: Polyglyceryl-4 Oleyl Ether), oleyl alcohol comprising 2 mol of glycerol (INCI name: Polyglyceryl-2 Oleyl Ether), cetearyl alcohol containing 2 mol of glycerol, cetearyl alcohol containing 6 mol of glycerol, oleyl/cetyl alcohol containing 6 mol of glycerol, and octadecanol containing 6 mol of glycerol.

Among the glycerolated alcohols, it is more particularly preferred to use a C8/C10 alcohol containing 1 mol of glycerol, a C10/C12 alcohol containing 1 mol of glycerol and a C12 alcohol containing 1.5 mol of glycerol.

The non-ionic surfactant(s) that may be used in the composition according to the invention are preferentially chosen from:

oxyethylenated $C_8$ to $C_{40}$ alcohols comprising from 1 to 100 mol of ethylene oxide, preferably from 2 to 50 and more particularly from 2 to 40 mol of ethylene oxide and comprising one or two fatty chains;
saturated or unsaturated oxyethylenated plant oils comprising from 1 to 100 and preferably from 2 to 50 mol of ethylene oxide;
($C_8$-$C_{30}$)alkyl(poly)glucosides, which are optionally oxyalkylenated (0 to 10 OE) and comprising 1 to 15 glucose units;
monoglycerolated or polyglycerolated $C_8$ to $C_{40}$ alcohols, comprising from 1 to 50 mol of glycerol and preferably from 1 to 10 mol of glycerol;
saturated or unsaturated, linear or branched, oxyalkylenated $C_8$ to $C_{30}$ fatty acid amides;
esters of saturated or unsaturated, linear or branched, $C_8$ to $C_{30}$ acids and of polyethylene glycols;
and mixtures thereof.

The composition according to the invention may comprise one or more cationic surfactants.

The term "cationic surfactant" is intended to mean a surfactant that is positively charged when it is contained in the composition according to the invention. This surfactant may bear one or more positive permanent charges or may contain one or more cationizable functions in the composition according to the invention.

The cationic surfactant(s) are preferably chosen from primary, secondary or tertiary fatty amines, which are optionally polyoxyalkylenated, or salts thereof, and quaternary ammonium salts, and mixtures thereof.

The fatty amines generally comprise at least one $C_8$ to $C_{30}$ hydrocarbon-based chain.

By way of quaternary ammonium salts, mention may in particular be made of quaternary ammonium salts such as tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, the palmitylamidopropyltrimethylammonium salt, the stearamidopropyltrimethylammonium salt, the stearamidopropyldimethylcetearylammonium salt, or the stearamidopropyldimethyl(myristyl acetate)ammonium salt sold under the name Ceraphyl® 70 by the company Van Dyk. It is preferable in particular to use the chloride salts of these compounds;

quaternary ammonium salts of imidazoline, for example sold under the name Rewoquat® W 75 by the company Rewo;

di- or triquaternary ammonium salts, for example, Finquat CT-P available from the company Finetex (Quaternium 89), and Finquat CT, available from the company Finetex (Quaternium 75);

quaternary ammonium salts containing at least one ester function, such as the diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl groups preferably contain 14 to 18 carbon atoms and are obtained more particularly from a plant oil such as palm oil or sunflower oil. When the compound contains several acyl groups, these groups may be identical or different.

Such compounds are sold, for example, under the names Dehyquart® by the company Henkel, Stepanquat® by the company Stepan, Noxamium® by the company CECA or Rewoquat® WE 18 by the company Rewo-Witco.

Use may also be made of the ammonium salts containing at least one ester function that are described in patents U.S. Pat. No. 4,874,554 and U.S. Pat. No. 4,137,180.

Use may be made of behenoylhydroxypropyltrimethylammonium chloride sold by KAO under the name Quatarmin BTC 131.

Preferably, the ammonium salts comprising at least one ester function comprise two ester functions.

Among the quaternary ammonium salts containing at least one ester function, which may be used, it is preferred to use dipalmitoylethylhydroxyethylmethylammonium salts.

The composition according to the invention may comprise one or more anionic surfactants.

The term "anionic surfactant" is intended to mean a surfactant comprising, as ionic or ionizable groups, only anionic groups. These anionic groups are preferably chosen from the groups —COOH, —COO$^-$, —SO$_3$H, —SO$_3^-$, —OSO$_3$H, —OSO$_3^-$, —PO$_2$H$_2$, —PO$_2$H$^-$, —PO$_2^{2-}$, —P(OH)$_2$, =P(O)OH, —P(OH)O$^-$, =P(O)O$^-$, =POH, =PO$^-$, the anionic parts comprising a cationic counterion such as those of an alkali metal, an alkaline-earth metal or an ammonium.

As examples of anionic surfactants that may be used in the composition according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulfosuccinamates, acylisethionates and N-acyltaurates, polyglucoside polycarboxylic acid and alkyl monoester salts, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds comprising from 6 to 40 carbon atoms and the aryl group denoting a phenyl group.

These compounds may be oxyethylenated and then preferably comprise from 1 to 50 ethylene oxide units.

The salts of $C_6$-$C_{24}$ alkyl monoesters of polyglucoside-polycarboxylic acids may be chosen from $C_6$-$C_{24}$ alkyl polyglucoside-citrates, $C_6$-$C_{24}$ alkyl polyglucoside-tartrates and $C_6$-$C_{24}$ alkyl polyglucoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may in particular be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Use is preferably made of alkali metal or alkaline-earth metal salts and in particular of sodium or magnesium salts.

Among the anionic surfactants mentioned, ($C_6$-$C_{24}$)alkyl sulfates, ($C_6$-$C_{24}$)alkyl ether sulfates comprising from 2 to 50 ethylene oxide units, in particular in the form of alkali metal, ammonium, amino alcohol and alkaline-earth metal salts, or a mixture of these compounds, are preferably used.

In particular, ($C_{12}$-$C_{20}$)alkyl sulfates, ($C_{12}$-$C_{20}$)alkyl ether sulfates comprising from 2 to 20 ethylene oxide units, in particular in the form of alkali metal, ammonium, amino alcohol and alkaline-earth metal salts, or a mixture of these compounds, are preferably used. Even better still, it is preferred to use sodium lauryl ether sulfate containing 2.2 mol of ethylene oxide.

The composition according to the invention may comprise one or more amphoteric or zwitterionic surfactants.

In particular, the amphoteric or zwitterionic surfactant(s), which are preferably non-silicone, which may be used in the composition according to the present invention may in particular be derivatives of optionally quaternized aliphatic secondary or tertiary amines, in which derivatives the aliphatic group is a linear or branched chain comprising from 8 to 22 carbon atoms, said amine derivatives containing at least one anionic group, for instance a carboxylate, sulfonate, sulfate, phosphate or phosphonate group.

Mention may in particular be made of ($C_8$-$C_{20}$)alkylbetaines, ($C_8$-$C_{20}$)alkylsulfobetaines, ($C_8$-$C_{20}$)alkylamido($C_3$-$C_8$)alkylbetaines and ($C_8$-$C_{20}$)alkylamido($C_6$-$C_8$)alkylsulfobetaines.

Among the optionally quaternized, secondary or tertiary aliphatic amine derivatives that can be used, mention may be made of the compounds classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Mention may be made of the compound classified in the CTFA dictionary under the name sodium diethylaminopropyl cocoaspartamide and sold by the company Chimex under the name Chimexane HB.

These compounds may be used alone or as mixtures.

Among the amphoteric or zwitterionic surfactants mentioned above, use is preferably made of ($C_8$-$C_{20}$)alkylbetaines such as cocoylbetaine, ($C_8$-$C_{20}$)alkylamido($C_3$-$C_8$) alkylbetaines such as cocamidopropylbetaine, and mixtures thereof, and the compounds of formula (VIII) such as the sodium salt of diethylaminopropyl laurylaminosuccinamate (INCI name: sodium diethylaminopropyl cocoaspartamide).

Preferably, the composition according to the invention comprises one or more surfactants. More preferentially, the composition according to the invention comprises one or more surfactants chosen from non-ionic, anionic or amphoteric surfactants, and mixtures thereof.

Particularly preferably, the composition according to the invention comprises one or more non-ionic surfactants.

The total amount of surfactant(s), present in the composition according to the invention, can range from 0.1% to 25% by weight, and preferably from 0.5% to 20% by weight, relative to the total weight of the composition.

Alkaline Agents

The composition according to the invention may optionally also comprise one or more alkaline agents.

Preferably, the dye composition comprises one or more organic or mineral alkaline agents.

The mineral alkaline agent(s) are preferably chosen from aqueous ammonia, alkali metal carbonates or bicarbonates such as sodium or potassium carbonates and sodium or potassium bicarbonates, sodium hydroxide or potassium hydroxide, or mixtures thereof.

The organic alkaline agent(s) are preferably chosen from organic amines with a pKb at 25° C. of less than 12, preferably less than 10 and even more advantageously less than 6. It should be noted that it is the pKb corresponding to the highest basicity function. In addition, the organic amines do not comprise any alkyl or alkenyl fatty chain comprising more than ten carbon atoms.

The organic alkaline agent(s) are chosen, for example, from alkanolamines, oxyethylenated and/or oxypropylenated ethylenediamines, amino acids and the compounds of formula (IX) below:

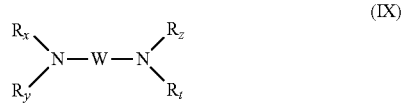

(IX)

in which formula (IX) W is a divalent $C_1$ to $C_6$ alkylene radical optionally substituted with one or more hydroxyl groups or a $C_1$ to $C_6$ alkyl radical and/or optionally interrupted with one or more heteroatoms, such as O, or $NR_u$, and $R_x$, $R_y$, $R_z$, $R_t$ and $R_u$, which are identical or different, represent a hydrogen atom or a $C_1$ to $C_6$ alkyl, $C_1$ to $C_6$ hydroxyalkyl or $C_1$ to $C_6$ aminoalkyl radical.

Examples of amines of formula (IX) that may be mentioned include 1,3-diaminopropane, 1,3-diamino-2-propanol, spermine and spermidine.

The term "alkanolamine" is intended to mean an organic amine comprising a primary, secondary or tertiary amine function, and one or more linear or branched $C_1$ to $C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane.

More particularly, the amino acids that may be used are of natural or synthetic origin, in their L, D or racemic form, and comprise at least one acid function chosen more particularly from carboxylic acid, sulfonic acid, phosphonic acid and phosphoric acid functions. The amino acids may be in neutral or ionic form.

As amino acids that may be used in the present invention, mention may be made in particular of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are, for example, histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made in particular of carnosine, anserine and balenine.

The organic amine may also be chosen from compounds comprising a guanidine function. As amines of this type that may be used in the present invention, besides arginine, which has already been mentioned as an amino acid, mention may be made in particular of creatine, creatinine, 1,1-dimethylguanidine, 1,1-diethylguanidine, glycocyamine, metformin, agmatine, n-amidinoalanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the alkaline agent(s) present in the composition according to the invention are chosen from aqueous ammonia, alkanolamines and amino acids in neutral or ionic form, in particular basic amino acids.

More preferentially, the alkaline agent(s) present in the composition according to the invention are chosen from aqueous ammonia, alkanolamines, and mixtures thereof. According to one particular embodiment, the alkaline agent is an organic agent, preferably an alkanolamine. When the alkaline agent is an alkanolamine, it is chosen from monoethanolamine.

The total amount of alkaline agent(s) present in the composition according to the invention may range from 0.01% to 30% by weight, and preferably from 0.1% to 20% by weight relative to the total weight of the ready-to-use composition.

The composition according to the invention may optionally also comprise one or more organic solvents.

By way of organic solvent, mention may for example be made of linear or branched $C_2$ to $C_4$ alkanols, such as ethanol and isopropanol; glycerol; polyols and polyol ethers such as 2-butoxyethanol, propylene glycol, hexylene glycol, dipropylene glycol, propylene glycol monomethyl ether, and diethylene glycol monoethyl ether and monomethyl ether, and also aromatic alcohols or ethers, such as benzyl alcohol or phenoxyethanol, and mixtures thereof.

The organic solvent(s) may be present in an amount ranging from 0.01% to 30% by weight, preferably ranging from 2% to 25% by weight, relative to the total weight of the composition.

The composition according to the invention may also optionally comprise one or more additives, different from the compounds of the invention and among which mention may be made of cationic, anionic, non-ionic or amphoteric polymers or mixtures thereof, antidandruff agents, antiseborrhoea agents, agents for preventing hair loss and/or for promoting hair regrowth, vitamins and provitamins including panthenol, sunscreens, mineral or organic pigments, sequestrants, plasticizers, solubilizers, acidifying agents, mineral or organic thickeners, in particular polymeric thickeners, opacifiers or nacreous agents, antioxidants, hydroxy acids, fragrances, preservatives, pigments and ceramides.

Needless to say, those skilled in the art will take care to select this or these optional additional compound(s) such that the advantageous properties intrinsically associated with the composition according to the invention are not, or are not substantially, adversely affected by the envisaged addition(s).

The above adjuvants may generally be present in an amount comprised, for each of them, of between 0 and 20% by weight relative to the total weight of the ready-to-use composition.

Chemical Oxidizing Agent

According to one particular embodiment of the invention, the composition according to the invention comprises at least one chemical oxidizing agent.

The expression "chemical oxidizing agent" is intended to mean an oxidizing agent other than atmospheric oxygen.

In particular, the chemical oxidizing agent(s) are chosen, for example, from hydrogen peroxide, urea peroxide, alkali metal bromates, peroxygenated salts, such as for example persulfates or perborates, peracids and precursors thereof and alkali metal or alkaline-earth metal percarbonates. Advantageously, the oxidizing agent is hydrogen peroxide.

The chemical oxidizing agent(s) may be present in a content ranging from 0.5% to 20%, better still from 1% to 15% by weight relative to the total weight of the composition.

Fatty Substances

According to one particular embodiment, the composition according to the invention comprises one or more fatty substances different from salified fatty acids.

The term "fatty substance" is intended to mean an organic compound that is insoluble in water at ambient temperature (25° C.) and at atmospheric pressure ($1.013 \times 10^5$ Pa) (solubility of less than 5% by weight, and preferably less than 1% by weight, even more preferably less than 0.1% by weight). They bear in their structure at least one hydrocarbon-based chain comprising at least 6 carbon atoms and/or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The term "oil" is intended to mean a "fatty substance" that is liquid at ambient temperature (25° C.) and at atmospheric pressure ($1.013 \times 10^5$ Pa).

The term "non-silicone fatty substance" is intended to mean a fatty substance not containing any Si-O bonds and the term "silicone fatty substance" is intended to mean a fatty substance containing at least one Si—O bond.

The fatty substances used in the composition according to the invention are different from salified fatty acids, i.e. they can be present in the composition in the form of free fatty acids.

In other words, the fatty substances of the invention do not contain any salified carboxylic acid groups (—C(O)O—). Particularly, the fatty substances of the invention are neither polyoxyalkylenated nor polyglycerolated.

Preferably, the fatty substances are different from salified fatty acids.

Preferably, the composition according to the invention comprises one or more fatty substances that are liquid at ambient temperature and atmospheric pressure ($1.013 \times 10^5$ Pa), different from salified fatty acids.

More particularly, the liquid fatty substances according to the invention are chosen from $C_6$-$C_{16}$ liquid hydrocarbons, liquid hydrocarbons comprising more than 16 carbon atoms, non-silicone oils of animal origin, oils of triglyceride type of plant or synthetic origin, fluoro oils, liquid fatty alcohols, liquid fatty acid and/or fatty alcohol esters other than triglycerides, and silicone oils, and mixtures thereof.

It is recalled that the fatty alcohols and esters more particularly contain at least one saturated or unsaturated, linear or branched hydrocarbon-based group, comprising 6 to 30 and better still from 8 to 30 carbon atoms, which is optionally substituted, in particular, with one or more hydroxyl groups (in particular 1 to 4). If they are unsaturated, these compounds may comprise one to three conjugated or unconjugated carbon-carbon double bonds.

As regards the $C_6$ to $C_{16}$ liquid hydrocarbons, they are linear, branched or optionally cyclic, and are preferably alkanes. Examples that may be mentioned include hexane, cyclohexane, undecane, dodecane, isododecane, tridecane or isoparaffins, such as isohexadecane or isodecane, and mixtures thereof.

The liquid hydrocarbons comprising more than 16 carbon atoms may be linear or branched, and of mineral or synthetic origin, and are preferably chosen from liquid paraffins or liquid petroleum jelly, polydecenes, hydrogenated polyisobutylene such as Parléam®, and mixtures thereof.

A hydrocarbon-based oil of animal origin that may be mentioned is perhydrosqualene.

The triglyceride oils of plant or synthetic origin are preferably chosen from liquid fatty acid triglycerides comprising from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil, and mixtures thereof.

The liquid fatty alcohols that are suitable for use in the invention are more particularly chosen from linear or branched, saturated or unsaturated, preferably unsaturated or branched, alcohols comprising from 6 to 30 carbon atoms and preferably from 8 to 30 carbon atoms. Examples that may be mentioned include octyldodecanol, 2-butyloctanol, 2-hexyldecanol, 2-undecylpentadecanol, isostearyl alcohol, oleyl alcohol, linolenyl alcohol, ricinoleyl alcohol, undecylenyl alcohol and linoleyl alcohol, and mixtures thereof.

As regards the liquid esters of fatty acids and/or of fatty alcohols other than the triglycerides mentioned above, mention may be made in particular of esters of saturated or unsaturated, linear $C_1$ to $C_{26}$ or branched $C_3$ to $C_{26}$ aliphatic monoacids or polyacids and of saturated or unsaturated, linear $C_1$ to $C_{26}$ or branched $C_3$ to $C_{26}$ aliphatic monoalcohols or polyalcohols, the total carbon number of the esters being greater than or equal to 6 and more advantageously greater than or equal to 10.

Preferably, for the esters of monoalcohols, at least one from among the alcohol and the acid from which the esters of the invention are derived is branched.

Among the monoesters, mention may be made of dihydroabietyl behenate; octyldodecyl behenate; isocetyl behenate; isostearyl lactate; lauryl lactate; linoleyl lactate; oleyl lactate; isostearyl octanoate; isocetyl octanoate; octyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; octyl isononanoate; 2-ethylhexyl isononate; octyldodecyl erucate; oleyl erucate; ethyl palmitate, isopropyl palmitate, 2-ethylhexyl palmitate, 2-octyldecyl palmitate, alkyl myristates such as isopropyl 2-octyldodecyl myristate, isobutyl stearate; 2-hexyldecyl laurate, and mixtures thereof.

Preferably, among the monoesters of monoacids and of monoalcohols, use will be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate, and mixtures thereof.

Still within the context of this variant, esters of $C_4$ to $C_{22}$ dicarboxylic or tricarboxylic acids and of $C_1$ to $C_{22}$ alcohols and esters of mono-, di- or tricarboxylic acids and of $C_2$ to $C_{26}$ di-, tri-, tetra- or pentahydroxy alcohols may also be used.

Mention may be made in particular of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates, and mixtures thereof.

The composition may also comprise, as fatty ester, sugar esters and diesters of $C_6$ to $C_{30}$ and preferably $C_{12}$ to $C_{22}$ fatty acids. It is recalled that the term "sugar" is intended to mean oxygen-bearing hydrocarbon-based compounds bearing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar esters of fatty acids may be chosen in particular from the group comprising the esters or mixtures of esters of sugars described previously and of linear or branched, saturated or unsaturated $C_6$ to $C_{30}$ and preferably $C_{12}$ to $C_{22}$ fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters may be, for example, oleates, laurates, palmitates, myristates, behenates, cocoates, stearates, linoleates, linolenates, caprates, arachidonates or mixtures thereof such as, in particular, the mixed esters oleo-palmitate, oleo-stearate and palmito-stearate.

More particularly, use is made of monoesters and diesters and in particular sucrose, glucose or methylglucose mono- or dioleates, stearates, behenates, oleopalmitates, linoleates, linolenates and oleostearates, and mixtures thereof.

An example that may be mentioned is the product sold under the name Glucate® DO by the company Amerchol, which is a methylglucose dioleate.

Preferably, use will be made of a liquid ester of a monoacid and of a monoalcohol.

The liquid fatty substance(s) is (are) preferentially chosen from liquid hydrocarbons containing more than 16 carbon atoms, vegetable oils, liquid fatty alcohols and liquid fatty esters, silicone oils and mixtures thereof.

Preferentially, the liquid fatty substance(s) is (are) chosen from liquid hydrocarbons comprising more than 16 carbon atoms, in particular liquid petroleum jelly.

In this particular embodiment, preferably, the total amount of fatty substance(s) present in the composition according to the invention is greater than or equal to 20% by weight, more preferentially greater than or equal to 30% by weight, and better still greater than or equal to 35% by weight, relative to the total weight of the composition.

More preferentially, in this particular embodiment, the total amount of fatty substance(s) present in the composition according to the invention ranges from 30% to 80%, and preferably from 30% to 70% by weight relative to the total weight of the composition.

Even more preferentially, in this particular embodiment, the total amount of liquid fatty substance(s) present in the composition according to the invention is greater than or equal to 20% by weight, more preferentially greater than or equal to 30% by weight, and better still greater than or equal to 35% by weight, relative to the total weight of the composition.

Even better still, in this particular embodiment, the total amount of liquid fatty substance(s) present in the composition according to the invention ranges from 30% to 80% by weight, and preferably from 30% to 70% by weight relative to the total weight of the composition.

When the composition of the invention contains at least one alkaline agent and at least one oxidizing agent, the composition is then ready to use. It can be applied to the hair so as to allow the keratin fibres to be dyed.

When the composition of the invention contains the alkaline agent and the oxidizing agent, it preferably contains at least 20% of fatty substances, preferably liquid fatty substances, preferably at least 30% by weight relative to the total weight of the composition. Preferably, this ready-to-use composition contains between 30% and 55% of fatty substances, preferably liquid fatty substances, preferably between 35% and 50%.

Process of the Invention

Another subject of the invention is a process for dyeing human keratin fibres, in particular the hair, comprising the application to the keratin fibres of the composition according to the invention.

According to one preferred embodiment, the composition contains at least one alkaline agent and at least one oxidizing agent. The composition is then applied to the keratin fibres and left on for approximately 3 to 50 minutes, preferably approximately 5 to 40 minutes, then there follows a step of rinsing, washing with a shampoo, again rinsing and, finally, drying.

If the composition of the invention is not mixed before application with the alkaline agent and the oxidizing agent, the various compositions can be applied sequentially, in any order, with or without intermediate rinsing.

According to another embodiment, the composition according to the invention results from the mixing of at least two compositions:

a dye composition comprising at least one oxidation base of formula (I), (II) or (III) described above, at least one 2-amino-5-ethylphenol coupler and at least one alkaline agent, and a composition comprising one or more chemical oxidizing agents.

Multi-Compartment Device:

Another subject of the invention is a multi-compartment device, preferably comprising at least two compartments, for dyeing keratin fibres, at least one first compartment containing the dye composition (A) according to the invention and at least one second compartment containing the oxidizing composition (B) as described above.

Finally, the present invention relates to the use of a composition as described above, for dyeing keratin fibres, and in particular the hair.

According to the present application, the term "keratin fibres" denotes human keratin fibres and in particular the hair.

The examples that follow serve to illustrate the invention without, however, being limiting in nature.

EXAMPLES

In the examples that follow, all the amounts are given as percentages by weight relative to the total weight of the composition. Unless otherwise indicated, the amounts are indicated in g % of Active Material (unless otherwise mentioned).

| Oxidizing composition | Ox1 |
|---|---|
| DIETHYLENETRIAMINEPENTAACETIC ACID | 0.06 |
| HYDROGEN PEROXIDE | 6 |
| DISODIUM TIN HEXAHYDROXIDE | 0.04 |
| TETRASODIUM PYROPHOSPHATE•10 H$_2$O | 0.02 |
| WATER | Qs 100 g |
| GLYCEROL | 0.5 |
| (50% LINEAR 70/30 C13/C15) ALKYL ETHER CARBOXYLIC ACID MONOETHANOL-AMIDE (2 OE) | 0.85 |
| CETYLSTEARYL ALCOHOL/OXYETHYLENATED CETYLSTEARYL ALCOHOL (30 OE) MIXTURE | 2.85 |
| PHOSPHORIC ACID | qs pH = 2.2 ± 0.2 |

The dye formulas A, B and C are mixed with the oxidizing formula Ox1 according to the ratio 1+1.5.

The mixtures thus obtained are applied to natural hair containing 90% grey hairs. After a leave-on time of 35 minutes, the locks are rinsed with clear water, then washed with a shampoo. Finally, the locks are dried.

After drying, the colouration obtained is evaluated using a Minolta CM2600D spectrocolorimeter (illuminant D65, angle 10°, specular component included) in the CIELab system. In this system, L* represents the lightness: the lower the value of L*, the more powerful the colouration obtained. C* represents the chromaticity and is obtained via the equation: $C^* = (a^{*2} + b^{*2})^{1/2}$ The higher the value of C*, the more chromatic the colouration obtained. The results are reported in the table below.

| Dye composition | formula A | formula B | formula C |
|---|---|---|---|
| DIETHYLENETRIAMINEPENTAACETICACID, PENTASODIUM SALT | 0.8 | 0.8 | 0.8 |
| AMMONIUM HYDROXIDE | 4.6 | 4.6 | 4.6 |
| POWDERED SODIUM METABISULFITE | 0.71 | 0.71 | 0.71 |
| PURE MONOETHANOLAMINE | 1.2 | 1.2 | 1.2 |
| (NON-TREATED ANATASE) TITANIUM OXIDE COATED WITH POLYDIMETHYLSILOXANE (98/2) (CI: 77891) | 0.15 | 0.15 | 0.15 |
| 2,3-DIAMINO-6,7-DIHYDRO-1H,5H-PYRAZOLO[1,2-A]PYRAZOL-1-ONE DIMETHANESULFONATE | — | 3 × 10$^{-3}$ mol | — |
| 2-[(3-AMINOPYRAZOLO[1,5-A]PYRIDIN-2-YL)OXY]ETHANOL HYDROCHLORIDE | 3 × 10$^{-3}$ mol | — | — |
| 2-AMINO-5-ETHYLPHENOL HCL (A158) | 3 × 10$^{-3}$ mol | 3 × 10$^{-3}$ mol | 3 × 10$^{-3}$ mol |
| 4-(3-AMINOPYRAZOLO[1,5-a]PYRIDIN-2-YL)-1,1-DIMETHYLPIPERAZIN-1-IUM CHLORIDE HYDROCHLORIDE | — | — | 3 × 10$^{-3}$ mol |
| GLYCOL DISTEARATE | 2 | 2 | 2 |
| CETYLSTEARYL ALCOHOL (50/50 C16/C18) | 11.5 | 11.5 | 11.5 |
| FRAGRANCE | 0.75 | 0.75 | 0.75 |
| POLY[(DIMETHYLIMINO)-1,3-PROPANEDIYL(DIMETHYLIMINO)-1,6-HEXANEDIYL DICHLORIDE] | 3 | 3 | 3 |
| DIMETHYLDIALLYL AMMONIUM CHLORIDE/ACRYLIC ACID COPOLYMER (80/20) | 1.52 | 1.52 | 1.52 |
| CARBOXYVINYL POLYMER SYNTHESIZED IN AN ETHYL ACETATE/CYCLOHEXANE MIXTURE | 0.4 | 0.4 | 0.4 |
| WATER | qs 100 | qs 100 | qs 100 |
| PROPYLENE GLYCOL | 10 | 10 | 10 |
| NATURAL LAURIC ACID | 3 | 3 | 3 |
| OXYETHYLENATED LAURYL ALCOHOL (12OE) | 7 | 7 | 7 |
| OXYETHYLENATED DECYL ALCOHOL (3 OE) | 9 | 9 | 9 |
| OXYETHYLENATED OLEOCETYL ALCOHOL (30 OE) | 4 | 4 | 4 |
| VITAMIN C: ASCORBIC ACID | 0.25 | 0.25 | 0.25 |

| composition | L* | a* | b* | C* | Shade |
|---|---|---|---|---|---|
| A + Ox1 | 27.36 | 9.99 | −9.11 | 13.52 | Strong Violet |
| B + Ox1 | 65.25 | 2.11 | 42.96 | 43.01 | Strong Yellow |
| C + Ox1 | 43.22 | −12.34 | 10.16 | 15.99 | Strong Green |

Comparative Example a) Dye Compositions

The dye compositions A1 and A2 were prepared from the ingredients of which the contents are indicated in the table below in g % of active material (unless otherwise mentioned).

| | A1 (invention) | A2 (comparative) |
|---|---|---|
| AMMONIUM HYDROXIDE | 4.6 | 4.6 |
| TITANIUM DIOXIDE | 0.15 | 0.15 |
| PENTASODIUM PENTETATE | 0.8 | 0.8 |
| ETHANOLAMINE | 1.2 | 1.2 |
| LAURIC ACID | 3 | 3 |
| 2-AMINO-5-ETHYLPHENOL HCL | $3.12 \times 10^{-3}$ mol | $3.12 \times 10^{-3}$ mol |
| 1-HYDROXYETHYL 4,5-DIAMINOPYRAZOLE SULFATE | | $3.12 \times 10^{-3}$ mol |
| 2-[(3-AMINOPYRAZOLO[1,5-A]PYRIDIN-2-YL)OXY]ETHANOL HYDROCHLORIDE | $3.12 \times 10^{-3}$ mol | |
| ASCORBIC ACID | 0.25 | 0.25 |
| POLYQUATERNIUM-22 | 1.5 | 1.5 |
| PROPYLENE GLYCOL | 10 | 10 |
| GLYCOL DISTEARATE | 2 | 2 |
| DECETH-3 | 9 | 9 |
| CETEARYL ALCOHOL | 11.5 | 11.5 |
| HEXADIMETHRINE CHLORIDE | 3 | 3 |
| LAURETH-12 | 7 | 7 |
| SILICA DIMETHYL SILYLATE | 1.2 | 1.2 |
| OLETH-30 | 4 | 4 |
| SODIUM METABISULFITE | 0.7 | 0.7 |
| CARBOMER | 0.4 | 0.4 |
| WATER | qs 100 | qs 100 |

Compositions A1 and A2 are mixed with the oxidizing composition Ox1 in a 1:1.5 weight ratio.

The mixture is thus obtained, A1+Ox1 and A2+Ox1, are applied to locks of natural hair containing 90% grey hairs.

After a leave-on time of 35 minutes, the locks are rinsed with clear water, then washed with a shampoo. Finally, the locks are dried.

The colorimetric measurements are performed using a Minolta CM2006D spectrocolorimeter (illuminant D65, angle 10°, specular component included) in the CIELab system. In this system, L* represents the lightness: the lower the value of L*, the more powerful the colouration obtained.

| | L* |
|---|---|
| A1 + Ox1 (invention) | 26.4 |
| A2 + Ox1 (comparative) | 31.0 |

The composition according to the invention A1+Ox1 has a lower value of L*, thus a more powerful colouration, compared with comparative composition A2+Ox1.

The invention claimed is:

1. A composition for dyeing keratin fibers, comprising:
(A) at least one 2-amino-5-ethylphenol coupler, an addition salt thereof, or a solvate thereof,
(B) at least one pyrazole heterocyclic oxidation base chosen from:
A1) pyrazolopyridines according to formula (I) below, addition salts thereof, solvates thereof, or solvates of the salts thereof:

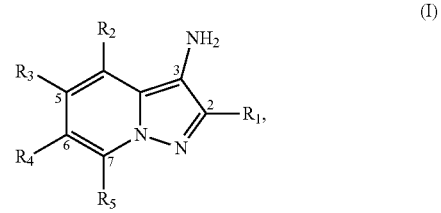

wherein:

$R_1$, $R_2$, $R_3$, $R_4$, and $R_5$, which may be identical or different, are chosen from a hydrogen atom; a halogen atom; a —NHSO$_3$H radical; a hydroxyl radical; a ($C_1$-$C_4$)alkyl radical; a ($C_1$-$C_4$)alkoxy radical; a ($C_1$-$C_4$)alkylthio radical; mono($C_1$-$C_4$)alkylamino; a di($C_1$-$C_4$)alkylamino radical, wherein the two alkyl groups may form, together with the nitrogen atom to which they are attached, a ring that may be interrupted with at least one nitrogen, oxygen, or sulfur atom; a heterocycle; a nitro radical; a phenyl radical; a carbonyl radical; a ($C_1$-$C_4$)alkoxycarbonyl radical; a carboxamido radical; a cyano radical; an amino radical; a sulfonyl radical; a —CO$_2$H radical, a —SO$_3$H radical, a —PO$_3$H$_2$ radical, a —PO$_4$H$_2$ radical, or a group:

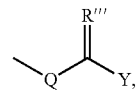

wherein R''' is chosen from an oxygen or nitrogen atom, Q is chosen from an oxygen atom, a NH group, or NH($C_1$-$C_4$)alkyl, and Y is chosen from a hydroxyl, amino, $C_1$-$C_4$ alkyl, ($C_1$-$C_4$)alkoxy, ($C_1$-$C_4$)alkylamino, or di($C_1$-$C_4$)alkylamino radical;

A2) pyrazolopyridine oxidation bases according to formula (II) below

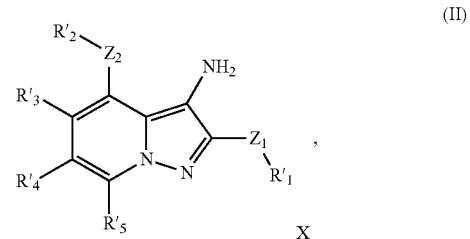

wherein:

$Z_1$ and $Z_2$, independently of each other, are chosen from:
a covalent single bond; or
a divalent radical chosen from:
a —O(CH$_2$)$_p$— radical, wherein p is chosen from an integer ranging from 0 to 6, or
a —NR'$_6$(CH$_2$)$_q$(C$_6$H$_4$)$_r$— radical, wherein q is chosen from an integer ranging from 0 to 6, t is chosen from 0 or 1, and R'$_6$ is chosen from a hydrogen atom or a $C_1$-$C_6$ alkyl radical optionally substituted with at least one hydroxyl group;

$Z_1$ may also be chosen from a divalent radical —S—, —SO—, or —SO$_2$—, wherein R'$_1$ is a methyl radical;

R'$_1$ and R'$_2$, independently of each other, are chosen from:
- a hydrogen atom;
- a $C_1$-$C_{10}$ alkyl radical, which is optionally substituted and optionally interrupted with a heteroatom or a group chosen from O, N, Si, S, SO, or SO$_2$;
- a halogen;
- a SO$_3$H radical;
- a substituted or unsubstituted, saturated, unsaturated, or aromatic, 5- to 8-membered ring, optionally containing at least one heteroatom or group chosen from N, O, S, SO$_2$, or —CO—, wherein the ring is optionally cationic and/or substituted with a cationic radical; or
- a —N$^+$R$_{19}$R$_{18}$R$_{19}$ group, wherein R$_{17}$, R$_{18}$, and R$_{19}$ are linear or branched $C_1$-$C_5$ alkyls optionally substituted with at least one hydroxyl group;

wherein when $Z_1$ represents a covalent bond, then $R_1$ optionally represents:
- an optionally substituted $C_1$-$C_6$ alkylcarbonyl radical; or
- a radical —O—CO—R, —CO—O—R, NR—CO—R', or —CO—NRR', wherein R and R', independently of each other, are chosen from a hydrogen atom or an optionally substituted $C_1$-$C_6$ alkyl radical;

wherein when $Z_2$ represents a covalent bond, then $R_2$ optionally represents:
- an optionally substituted $C_1$-$C_6$ alkylcarbonyl radical; or
- a radical —O—CO—R, —CO—O—R, NR—CO—R', or —CO—NRR', wherein R and R', independently of each other, are chosen from a hydrogen atom or an optionally substituted $C_1$-$C_6$ alkyl radical;

R'$_3$, R'$_4$, and R'$_5$, which may be identical or different, are chosen from:
- a hydrogen atom;
- a hydroxyl radical;
- a $C_1$-$C_6$ alkoxy radical;
- a $C_1$-$C_6$ alkylthio radical;
- an amino radical;
- a monoalkylamino radical;
- a $C_1$-$C_6$ dialkylamino radical, wherein the alkyl radicals may form, with the nitrogen atom to which they are attached, a saturated or unsaturated, aromatic or nonaromatic, 5- to 8-membered heterocycle, which may contain at least one heteroatom or group chosen from N, O, S, SO$_2$, and CO, wherein the heterocycle is optionally cationic and/or substituted with a cationic radical;
- an optionally substituted $C_1$-$C_6$ alkylcarbonyl radical;
- a radical —O—CO—R, —CO—O—R, NR—CO—R', or —CO—NRR', wherein R and R' independently of each other, are chosen from a hydrogen atom or an optionally substituted $C_1$-$C_6$ alkyl radical;
- a halogen;
- a —NHSO$_3$H radical;
- an optionally substituted $C_1$-$C_4$ alkyl radical;
- a saturated, unsaturated or aromatic, optionally substituted carbon-based ring; or R'$_3$, R'$_4$, and R'$_5$ optionally form in pairs a partially saturated or unsaturated ring, and X is chosen from an ion or group of ions making it possible to ensure the electronegativity of the derivative of formula (II);

wherein least one of the groups R'$_1$ or R'$_2$ is chosen from a cationic radical; or A3) diamino-N,N-dihydropyrazolone derivatives according to formula (III) below, addition salts thereof, solvates thereof, or solvates of the salts thereof:

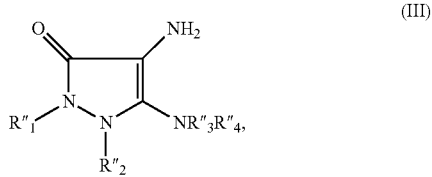

wherein:

R"$_3$ and R"$_4$, which may be identical or different, are chosen from:
- a hydrogen atom;
- a linear or branched $C_1$-$C_6$ alkyl radical optionally substituted with at least one radical chosen from a OR"$_5$ radical, a NR"$_6$R"$_7$ radical, a carboxyl radical, a sulfonic radical, a carboxamido CONR"$_6$R"$_7$ radical, a sulfonamido radical SO$_2$NR"$_6$R"$_7$, a heteroaryl, an aryl optionally substituted with at least one ($C_1$-$C_4$)alkyl, hydroxyl, $C_1$-$C_2$ alkoxy, amino, or (di)alkyl($C_1$-$C_2$)amino group;
- an aryl radical optionally substituted with at least one ($C_1$-$C_4$)alkyl, hydroxyl, $C_1$-$C_2$ alkoxy, amino, or (di)alkyl($C_1$-$C_2$)amino;
- a 5- or 6-membered heteroaryl radical, optionally substituted with at least one radical chosen from ($C_1$-$C_4$)alkyl or ($C_1$-$C_2$)alkoxy; or
- R"$_3$ and R"$_4$ optionally form, together with the nitrogen atom to which they are attached, a 5- or 7-membered heterocycle, the carbon atoms of which is optionally replaced with an optionally substituted oxygen or nitrogen atom;

R"$_5$, R"$_6$, and R"$_7$, which may be identical or different, are chosen from:
- a hydrogen atom;
- a linear or branched $C_1$-$C_4$ alkyl radical optionally substituted with at least one radical chosen from hydroxyl, $C_1$-$C_2$ alkoxy, carboxamido CONR"$_8$R"$_9$, sulfonyl SO$_2$R"$_8$, aryl optionally substituted with a ($C_1$-$C_4$)alkyl, hydroxyl, $C_1$-$C_2$ alkoxy, amino, or (di)alkyl($C_1$-$C_2$)amino, aryl optionally substituted with a ($C_1$-$C_4$)alkyl, hydroxyl, $C_1$-$C_2$ alkoxy, amino or (di)alkyl($C_1$-$C_2$)amino; or
- R"$_6$ and R"$_7$, which may be identical or different, are optionally chosen from a carboxamido radical CONR"$_8$R"$_9$ or a sulfonyl radical SO$_2$R"$_8$;

R"$_8$ and R"$_9$, which may be identical or different, are chosen from a hydrogen atom, a linear or branched $C_1$-$C_4$ alkyl radical optionally substituted with at least one hydroxyl or $C_1$-$C_2$ alkoxy; and R"$_1$ and R"$_2$ form, together with the nitrogen atom(s) to which they are attached, a saturated or unsaturated 5- to 7-membered heterocycle optionally substituted with at least one radical chosen from halogen atoms and amino, (di)alkyl($C_1$-$C_4$)amino, hydroxyl, carboxyl, carboxamido and ($C_1$-$C_2$)alkoxy radicals, $C_1$-$C_4$ alkyl radicals optionally substituted with at least one hydroxyl, amino, (di)alkylamino, alkoxy, carboxyl, or sulfonyl radical.

2. The composition according to claim 1, wherein the pyrazolopyridines of formula (I) are chosen from those according to the formula below:

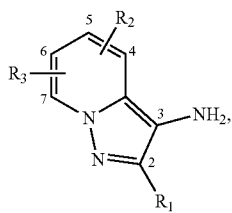

wherein:
R₁, R₂, and R₃, which may be identical or different, are chosen from a hydrogen atom; a halogen atom; a hydroxyl radical; a $(C_1-C_4)$alkyl radical; a $(C_1-C_4)$alkylthio radical; a $(C_1-C_4)$alkoxy radical; a —NHSO₃H radical; an amino radical; a $(C_1-C_4)$alkylamino radical; a di$(C_1-C_4)$alkylamino radical, wherein the two alkyl groups may form, together with the nitrogen atom to which they are attached, a ring that may be interrupted with at least one nitrogen, oxygen, or sulfur atom; a heterocycle; a sulfonamide radical; a carbonyl radical; a $(C_1-C_4)$alkoxycarbonyl radical; a carboxamido radical; or a group:

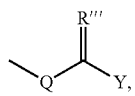

wherein R''' is chosen from an oxygen or nitrogen atom, Q is chosen from an oxygen atom, an NH group, or NH($C_1$-$C_4$)alkyl, and Y is chosen from a hydroxyl, amino, $C_1$-$C_4$ alkyl, $(C_1$-$C_4)$alkoxy, $(C_1$-$C_4)$alkylamino, or di(Ci-C4)alkylamino radical.

3. The composition according to claim 1, wherein the pyrazolopyridines of formula (I) are chosen from:
pyrazolo[1,5-a]pyridin-3-ylamine;
2-acetylaminopyrazolo[1,5-a]pyridin-3-ylamine;
2-morpholin-4-ylpyrazolo[1,5-a]pyridin-3-ylamine;
3-aminopyrazolo[1,5-a]pyridine-2-carboxylic acid;
2-methoxypyrazolo[1,5-a]pyridin-3-ylamino;
(3-aminopyrazolo[1,5-a]pyridin-7-yl)methanol;
2-(3-aminopyrazolo[1,5-a]pyridin-5-yl)ethanol;
2-(3-aminopyrazolo[1,5-a]pyridin-7-yl)ethanol;
(3-aminopyrazolo[1,5-a]pyridin-2-yl)methanol;
3,6-diaminopyrazolo[1,5-a]pyridine;
3,4-diaminopyrazolo[1,5-a]pyridine;
pyrazolo[1,5-a]pyridine-3,7-diamine;
7-morpholin-4-ylpyrazolo[1,5-a]pyridin-3-ylamine;
pyrazolo[1,5-a]pyridine-3,5-diamine;
5-morpholin-4-ylpyrazolo[1,5-a]pyridin-3-ylamine;
2-[(3-aminopyrazolo[1,5-a]pyridin-5-yl)(2-hydroxyethyl)amino]ethanol;
2-[(3-aminopyrazolo[1,5-a]pyridin-7-yl)(2-hydroxyethyl)amino]ethanol;
3-aminopyrazolo[1,5-a]pyridin-5-ol;
3-aminopyrazolo[1,5-a]pyridin-4-ol;
3-aminopyrazolo[1,5-a]pyridin-6-ol;
3-aminopyrazolo[1,5-a]pyridin-7-ol;
2-methoxy-6,7-dimethylpyrazolo[1,5-a]pyridin-3-amine;
2-[(3-aminopyrazolo[1,5-a]pyridin-2-yl)oxy]ethanol;
4-ethyl-2-methoxy-7-methylpyrazolo[1,5-a]pyridin-3-amine hydrochloride;
1-(3-aminopyrazolo[1,5-a]pyridin-2-yl)pyrrolidin-3-ol;
2,2'-[(3-aminopyrazolo[1,5-a]pyridin-2-yl)imino]diethanol;
2-[(3-aminopyrazolo[1,5-a]pyridin-2-yl)amino]ethanol;
N2-(2-pyridin-3-ylethyl)pyrazolo[1,5-a]pyridine-2,3-diamine; or
addition salts thereof, solvates thereof, or solvates of the salts thereof.

4. The composition according to claim 1, wherein the pyrazolopyridine oxidation bases are chosen from compounds according to formula (II) below:

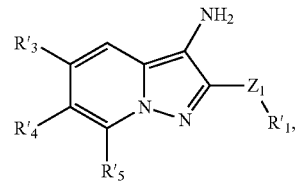

wherein:
$Z_1$ is chosen from:
a covalent single bond; or
a divalent radical chosen from:
a —O(CH₂)ₚ— radical, wherein p is chosen from an integer ranging from 0 to 6, or
a —NR'₆(CH₂)_q(C₆H₄)_t— radical, wherein q is chosen from an integer ranging from 0 to 6, t is chosen from 0 or 1, and R'₆ is chosen from a hydrogen atom or a $C_1$-$C_6$ alkyl radical optionally substituted with at least one hydroxyl group; or
a radical —S—, —SO—, or —SO₂—, wherein R'₁ is a methyl radical;
R'₁ is chosen from:
a hydrogen atom;
a $C_1$-$C_{10}$ alkyl radical, which is optionally substituted and optionally interrupted with a heteroatom or a group chosen from O, N, Si, S, SO, or SO₂;
a halogen;
a SO₃H radical;
a substituted or unsubstituted, saturated, unsaturated, or aromatic, 5- to 8-membered ring, optionally containing at least one heteroatom or group chosen from N, O, S, SO₂, or —CO—, wherein the ring is optionally cationic and/or substituted with a cationic radical; or
a —N⁺R₁₉R₁₈R₁₉ group, wherein R₁₇, R₁₈ and R₁₉ are linear or branched $C_1$-$C_5$ alkyls optionally substituted with at least one hydroxyl group;
wherein when $Z_1$ represents a covalent bond, then R₁ optionally represents:
an optionally substituted $C_1$-$C_6$ alkylcarbonyl radical;
a radical —O—CO—R, —CO—O—R, NR—CO—R', or —CO—NRR', wherein R and R', independently of each other, are chosen from a hydrogen atom or an optionally substituted $C_1$-$C_6$ alkyl radical;
wherein when $Z_2$ represents a covalent bond, then R₂ optionally represents:
an optionally substituted $C_1$-$C_6$ alkylcarbonyl radical; or
a radical —O—CO—R, —CO—O—R, NR—CO—R', or —CO—NRR', wherein R and R', independently of each other, are chosen from a hydrogen atom or an optionally substituted $C_1$-$C_6$ alkyl radical;
R'₃, R'₄, and R'₅, which may be identical or different, are chosen from:
a hydrogen atom;
a hydroxyl radical;
a $C_1$-$C_6$ alkoxy radical;
a $C_1$-$C_6$ alkylthio radical;
an amino radical;

a monoalkylamino radical;

a $C_1$-$C_6$ dialkylamino radical, wherein the alkyl radicals may form, with the nitrogen atom to which they are attached, a saturated or unsaturated, aromatic or nonaromatic, 5- to 8-membered heterocycle, which optionally contain at least one heteroatom or group chosen from N, O, S, $SO_2$, and CO, wherein the heterocycle is optionally cationic and/or substituted with a cationic radical;

an optionally substituted $C_1$-$C_6$ alkylcarbonyl radical;

a radical —O—CO—R, —CO—O—R, NR—CO—R', or —CO—NRR', wherein R and R', independently of each other, are chosen from a hydrogen atom or an optionally substituted $C_1$-$C_6$ alkyl radical;

a halogen;

a —$NHSO_3H$ radical;

an optionally substituted $C_1$-$C_4$ alkyl radical;

a saturated, unsaturated or aromatic, optionally substituted carbon-based ring; or $R'_3$, $R'_4$, and $R'_5$ optionally form in pairs a partially saturated or unsaturated ring.

5. The composition according to claim 1, wherein the compounds of formulae (I) and (II) are chosen from:

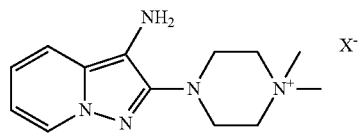

4-(3-Aminopyrazolo[1,5-a]pyridin-2-yl)-1,1-dimethylpiperazin-1-ium salt

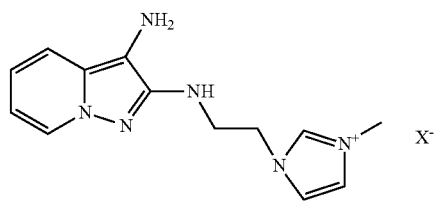

3-[2-(3-Aminopyrazolo[1,5-a]pyridin-2-ylamino)ethyl]-1-methyl-3H-imidazol-1-ium salt, 2-[(3-aminopyrazolo[1,5-a]pyridin-2-yl)oxy]ethanol, or addition salts thereof, solvates thereof, or solvates of the salts thereof.

6. The composition according to claim 1, wherein $R''_1$ and $R''_2$ form, together with the nitrogen atom(s) to which they are attached, an optionally substituted saturated or unsaturated 5- or 6-membered ring, optionally substituted with at least one $C_1$-$C_4$ alkyl radical, a hydroxyl, a $(C_1$-$C_2)$alkoxy, a carboxyl, a carboxamido, an amino, or a $(di)(C_1$-$C_2)$ alkylamino.

7. The composition according to claim 1, wherein $R''_3$ and $R''_4$ are chosen from a hydrogen atom; a linear or branched $C_1$-$C_6$ alkyl radical optionally substituted with at least one hydroxyl, $(C_1$-$C_2)$alkoxy, amino or $(di)(C_1$-$C_2)$alkylamino; or a phenyl radical optionally substituted with at least one hydroxyl, amino, or $(C_1$-$C_2)$alkoxy.

8. The composition according to claim 1, wherein the diamino-N,N-dihydropyrazolone derivatives according to formula (III) are chosen from:

2,3-diamino-6,7-dihydro-1H,5H-pyrazolo[1,2-a]pyrazol-1-one;

2-amino-3-ethylamino-6,7-dihydro-1H,5H-pyrazolo[1,2-a]pyrazol-1-one;

2-amino-3-isopropylamino-6,7-dihydro-1H,5H-pyrazolo[1,2-a]pyrazol-1-one;

2-amino-3-(pyrrolidin-1-yl)-6,7-dihydro-1H,5H-pyrazolo[1,2-a]pyrazol-1-one;

2-amino-3-(2-hydroxyethyl)amino-6,7-dihydro-1H,5H-pyrazolo[1,2-a]pyrazol-1-one;

2-amino-3-dimethylamino-6,7-dihydro-1H,5H-pyrazolo[1,2-a]pyrazol-1-one;

2,3-diamino-5,6,7,8-tetrahydro-1H,6H-pyridazino[1,2-a]pyrazol-1-one;

2,3-diamino-6-hydroxy-6,7-dihydro-1H,5H-pyrazolo[1,2-a]pyrazol-1-one; or addition salts thereof, solvates thereof, or solvates of the salts thereof.

9. The composition according to claim 1, further comprising at least one surfactant.

10. The composition according to claim 9, wherein the at least one surfactant is chosen from non-ionic surfactants.

11. The composition according to claim 1, further comprising at least one alkaline agent.

12. The composition according to claim 1, wherein the at least one pyrazole heterocyclic oxidation base is present in a total amount ranging from about 0.0001% to about 20% by weight, relative to the total weight of the composition.

13. The composition according to claim 1, wherein the at least one pyrazole heterocyclic oxidation base is present in a total amount ranging from about 0.005% to about 10% by weight, relative to the total weight of the composition.

14. The composition according to claim 1, further comprising at least one chemical oxidizing agent.

15. The composition according to claim 14, wherein the at least one chemical oxidizing agent is chosen from hydrogen peroxide.

16. A method for dyeing keratin fibers, comprising applying to the keratin fibers a dye composition, the dye composition comprising:

(A) at least one 2-amino-5-ethylphenol coupler, an addition salt thereof, or a solvate thereof, (B) at least one pyrazole heterocyclic oxidation base chosen from:

A1) pyrazolopyridines according to formula (I) below, addition salts thereof, solvates thereof, or solvates of the salts thereof:

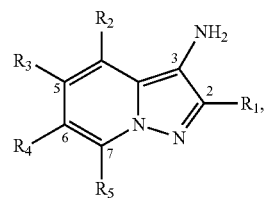

wherein:

$R_1$, $R_2$, $R_3$, $R_4$, and $R_5$, which may be identical or different, are chosen from a hydrogen atom, a halogen atom; a —$NHSO_3H$ radical, a hydroxyl radical, a $(C_1$-$C_4)$alkyl radical, a $(C_1$-$C_4)$alkoxy radical, a $(C_1$-$C_4)$alkylthio radical, mono$(C_1$-$C_4)$alkylamino, a di$(C_1$-$C_4)$alkylamino radical, wherein the two alkyl groups may form, together with the nitrogen atom to which they are attached, a ring that may be interrupted with at least one nitrogen, oxygen, or sulfur atom, a heterocycle, a nitro radical, a phenyl radical, a carbonyl radical; a (C₁-C₄)alkoxycarbonyl radical, a carboxamido radical, a cyano radical, an amino radical, a sulfonyl radical, a —CO₂H radical, a —SO₃H radical, a —PO₃H₂ radical, a —PO₄H₂ radical, or a group:

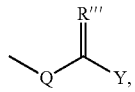

wherein R''' is chosen from an oxygen or nitrogen atom, Q is chosen from an oxygen atom, a NH group, or NH(C₁-C₄)alkyl, and Y is chosen from a hydroxyl, amino, C₁-C4 alkyl, (C₁-C₄)alkoxy, (C₁-C₄)alkylamino, or di(Ci-C4)alkylamino radical;

A2) pyrazolopyridine oxidation bases according to formula (II) below

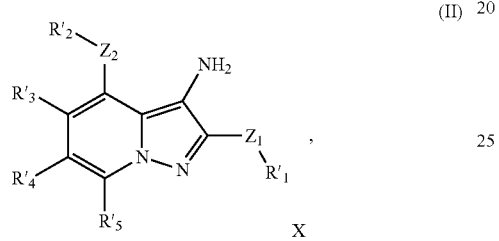

wherein:
$Z_1$ and $Z_2$, independently of each other, are chosen from:
  a covalent single bond; or
  a divalent radical chosen from:
    a —O(CH₂)ₚ— radical, wherein p is chosen from an integer ranging from 0 to 6, or
    a —NR'₆(CH₂)_q(C₆H₄)_t— radical, wherein q is chosen from an integer ranging from 0 to 6 and t is chosen from 0 or 1, and R'₆ is chosen from a hydrogen atom or a C₁-C₆ alkyl radical optionally substituted with at least one hydroxyl group;
$Z_1$ may also be chosen from a divalent radical —S—, —SO—, or —SO₂—, wherein R'₁ is a methyl radical;
R'₁ and R'₂, independently of each other, are chosen from:
  a hydrogen atom;
  a C₁-C₁₀ alkyl radical, which is optionally substituted and optionally interrupted with a heteroatom or a group chosen from O, N, Si, S, SO, or SO₂;
  a halogen;
  a SO₃H radical;
  a substituted or unsubstituted, saturated, unsaturated, or aromatic, 5- to 8-membered ring, optionally containing at least one heteroatom or group chosen from N, O, S, SO₂, or —CO—, wherein the ring is optionally cationic and/or substituted with a cationic radical; or
  a —N⁺R₁₉R₁₈R₁₉ group, wherein R₁₇, R₁₈, and R₁₉ are linear or branched C₁-C₅ alkyls optionally substituted with at least one hydroxyl group;
wherein when $Z_1$ represents a covalent bond, then $R_1$ optionally represents:
  an optionally substituted C₁-C₆ alkylcarbonyl radical; or
  a radical —O—CO—R, —CO—O—R, NR—CO—R', or —CO—NRR', wherein R and R', independently of each other, are chosen from a hydrogen atom or an optionally substituted C₁-C₆ alkyl radical;
wherein when $Z_2$ represents a covalent bond, then $R_2$ optionally represents:
  an optionally substituted C₁-C₆ alkylcarbonyl radical; or
  a radical —O—CO—R, —CO—O—R, NR—CO—R', or —CO—NRR', wherein R and R', independently of each other, are chosen from a hydrogen atom or an optionally substituted C₁-C₆ alkyl radical;
R'₃, R'₄, and R'₅, which may be identical or different, are chosen from:
  a hydrogen atom;
  a hydroxyl radical;
  a C₁-C₆ alkoxy radical;
  a C₁-C₆ alkylthio radical;
  an amino radical;
  a monoalkylamino radical;
  a C₁-C₆ dialkylamino radical, wherein the alkyl radicals may form, with the nitrogen atom to which they are attached, a saturated or unsaturated, aromatic or nonaromatic, 5- to 8-membered heterocycle, which may contain at least one heteroatom or group chosen from N, O, S, SO₂, and CO, wherein the heterocycle is optionally cationic and/or substituted with a cationic radical;
  an optionally substituted C₁-C₆ alkylcarbonyl radical;
  a radical —O—CO—R, —CO—O—R, NR—CO—R', or —CO—NRR', wherein R and R' independently of each other, are chosen from a hydrogen atom or an optionally substituted C₁-C₆ alkyl radical;
  a halogen;
  a —NHSO₃H radical;
  an optionally substituted C₁-C₄ alkyl radical;
  a saturated, unsaturated or aromatic, optionally substituted carbon-based ring; or
R'₃, R'₄, and R'₅ optionally form in pairs a partially saturated or unsaturated ring, and
X is chosen from an ion or group of ions making it possible to ensure the electronegativity of the derivative of formula (II);
wherein least one of the groups R'₁ or R'₂ is chosen from a cationic radical; or A3) diamino-N,N-dihydropyrazolone derivatives according to formula (III) below, addition salts thereof, solvates thereof, or solvates of the salts thereof:

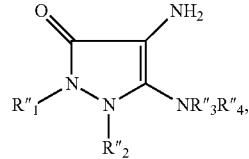

wherein:
R''₃ and R''₄, which may be identical or different, are chosen from:
  a hydrogen atom;
  a linear or branched C₁-C₆ alkyl radical optionally substituted with at least one radical chosen from a OR''₅ radical, a NR''₆R''₇ radical, a carboxyl radical, a sulfonic radical, a carboxamido CONR''₆R''₇ radical, a sulfonamido radical SO₂NR''₆R''₇, a heteroaryl, an aryl optionally substituted with at least one (C₁-C₄)alkyl, hydroxyl, C₁-C₂ alkoxy, amino, or (di)alkyl(C₁-C₂)amino group;
  an aryl radical optionally substituted with at least one (C₁-C₄)alkyl, hydroxyl, C₁-C₂ alkoxy, amino, or (di)alkyl(C₁-C₂)amino;

a 5- or 6-membered heteroaryl radical, optionally substituted with at least one radical chosen from (C$_1$-C$_4$)alkyl or (C$_1$-C$_2$)alkoxy; or R"$_3$ and R"$_4$ optionally form, together with the nitrogen atom to which they are attached, a 5- or 7-membered heterocycle, the carbon atoms of which is optionally replaced with an optionally substituted oxygen or nitrogen atom;

R"$_5$, R"$_6$, and R"$_7$, which may be identical or different, are chosen from:
  a hydrogen atom;
  a linear or branched C$_1$-C$_4$ alkyl radical optionally substituted with at least one radical chosen from hydroxyl, C$_1$-C$_2$ alkoxy, carboxamido CONR"$_8$R"$_9$, sulfonyl SO$_2$R"$_8$, aryl optionally substituted with a (C$_1$-C$_4$)alkyl, hydroxyl, C$_1$-C$_2$ alkoxy, amino, or (di)alkyl(C$_1$-C$_2$)amino, aryl optionally substituted with a (C$_1$-C$_4$)alkyl, hydroxyl, C$_1$-C$_2$ alkoxy, amino or (di)alkyl(C$_1$-C$_2$)amino; or
  R"$_6$ and R"$_7$, which may be identical or different, are optionally chosen from a carboxamido radical CONR"$_8$R"$_9$ or a sulfonyl radical SO$_2$R"$_8$;

R"$_8$ and R"$_9$, which may be identical or different, are chosen from a hydrogen atom, a linear or branched C$_1$-C$_4$ alkyl radical optionally substituted with at least one hydroxyl or C$_1$-C$_2$ alkoxy; and R"$_1$ and R"$_2$ form, together with the nitrogen atom(s) to which they are attached, a saturated or unsaturated 5- to 7-membered heterocycle optionally substituted with at least one radical chosen from halogen atoms and amino, (di)alkyl(C$_1$-C$_4$)amino, hydroxyl, carboxyl, carboxamido and (C$_1$-C$_2$)alkoxy radicals, C$_1$-C$_4$ alkyl radicals optionally substituted with at least one hydroxyl, amino, (di)alkylamino, alkoxy, carboxyl, or sulfonyl radicals.

17. A multi-compartment device for dyeing keratin fibers, comprising:
  at least one first compartment comprising a dye composition, wherein the dye composition comprises:
  (A) at least one 2-amino-5-ethylphenol coupler, an addition salt thereof, or a solvate thereof,
  (B) at least one pyrazole heterocyclic oxidation base chosen from:
    A1) pyrazolopyridines according to formula (I) below, addition salts thereof, solvates thereof, or solvates of the salts thereof:

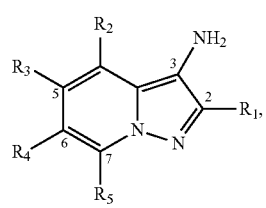

(I)

wherein:
R$_1$, R$_2$, R$_3$, R$_4$, and R$_5$, which may be identical or different, are chosen from a hydrogen atom, a halogen atom, a —NHSO$_3$H radical, a hydroxyl radical, a (C$_1$-C$_4$)alkyl radical, a (C$_1$-C$_4$)alkoxy radical, a (C$_1$-C$_4$)alkylthio radical, mono(C$_1$-C$_4$)alkylamino, a di(C$_1$-C$_4$)alkylamino radical, wherein the two alkyl groups may form, together with the nitrogen atom to which they are attached, a ring that may be interrupted with at least one nitrogen, oxygen, or sulfur atom, a heterocycle; a nitro radical; a phenyl radical, a carbonyl radical, a (C$_1$-C$_4$)alkoxycarbonyl radical, a carboxamido radical, a cyano radical, an amino radical, a sulfonyl radical, a —CO$_2$H radical, a —SO$_3$H radical, a —PO$_3$H$_2$ radical, a —PO$_4$H$_2$ radical, or a group:

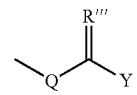

wherein R''' is chosen from an oxygen or nitrogen atom, Q is chosen from an oxygen atom, a NH group, or NH(C$_1$-C$_4$)alkyl, and Y is chosen from a hydroxyl, amino, C$_1$-C$_4$ alkyl, (C$_1$-C$_4$)alkoxy, (C$_1$-C$_4$)alkylamino, or di(C$_1$-C$_4$)alkylamino radical;

A2) pyrazolopyridine oxidation bases according to formula (II) below

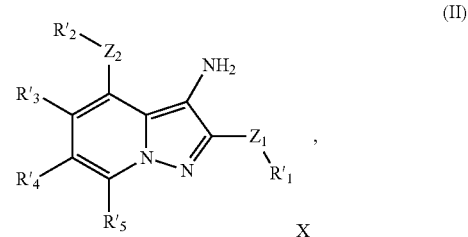

(II)

wherein:
Z$_1$ and Z$_2$, independently of each other, are chosen from:
  a covalent single bond; or
  a divalent radical chosen from:
    a —O(CH$_2$)$_p$— radical, wherein p is chosen from an integer ranging from 0 to 6, or
    a —NR'$_6$(CH$_2$)$_q$(C$_6$H$_4$)$_t$— radical, wherein q is chosen from an integer ranging from 0 to 6 and t is chosen from 0 or 1, and R'$_6$ is chosen from a hydrogen atom or a C$_1$-C$_6$ alkyl radical optionally substituted with at least one hydroxyl group;

Z$_1$ may also be chosen from a divalent radical —S—, —SO—, or —SO$_2$—, wherein R'$_1$ is a methyl radical;

R'$_1$ and R'$_2$, independently of each other, are chosen from:
  a hydrogen atom;
  a C$_1$-C$_{10}$ alkyl radical, which is optionally substituted and optionally interrupted with a heteroatom or a group chosen from O, N, Si, S, SO, or SO$_2$;
  a halogen;
  a SO$_3$H radical;
  a substituted or unsubstituted, saturated, unsaturated, or aromatic, 5- to 8-membered ring, optionally containing at least one heteroatom or group chosen from N, O, S, SO$_2$, or —CO—, wherein the ring is optionally cationic and/or substituted with a cationic radical; or
  a —N$^+$R$_{19}$R$_{18}$R$_{19}$ group, wherein R$_{17}$, R$_{18}$ and R$_{19}$ are linear or branched C$_1$-C$_5$ alkyls optionally substituted with at least one hydroxyl group;

wherein when Z$_1$ represents a covalent bond, then R$_1$ optionally represents:
  an optionally substituted C$_1$-C$_6$ alkylcarbonyl radical; or
  a radical —O—CO—R, —CO—O—R, NR—CO—R', or —CO—NRR', wherein R and R', independently of each other, are chosen from a hydrogen atom or an optionally substituted C$_1$-C$_6$ alkyl radical;

wherein when Z$_2$ represents a covalent bond, then R$_2$ optionally represents:

an optionally substituted $C_1$-$C_6$ alkylcarbonyl radical; or a radical —O—CO—R, —CO—O—R, NR—CO—R', or —CO—NRR', wherein R and R', independently of each other, are chosen from a hydrogen atom or an optionally substituted $C_1$-$C_6$ alkyl radical;

$R'_3$, $R'_4$ and $R'_5$, which may be identical or different, are chosen from:
a hydrogen atom;
a hydroxyl radical;
a $C_1$-$C_6$ alkoxy radical;
a $C_1$-$C_6$ alkylthio radical;
an amino radical;
a monoalkylamino radical;
a $C_1$-$C_6$ dialkylamino radical, wherein the alkyl radicals may form, with the nitrogen atom to which they are attached, a saturated or unsaturated, aromatic or nonaromatic, 5- to 8-membered heterocycle, which may contain at least one heteroatom or group chosen from N, O, S, $SO_2$, and CO, wherein the heterocycle is optionally cationic and/or substituted with a cationic radical;
an optionally substituted $C_1$-$C_6$ alkylcarbonyl radical;
a radical —O—CO—R, —CO—O—R, NR—CO—R', or —CO—NRR', wherein R and R' independently of each other, are chosen from a hydrogen atom or an optionally substituted $C_1$-$C_6$ alkyl radical;
a halogen;
a —$NHSO_3H$ radical;
an optionally substituted $C_1$-$C_4$ alkyl radical;
a saturated, unsaturated or aromatic, optionally substituted carbon-based ring; or
$R'_3$, $R'_4$, and $R'_5$ optionally form in pairs a partially saturated or unsaturated ring, and X is chosen from an ion or group of ions making it possible to ensure the electronegativity of the derivative of formula (II);

wherein least one of the groups $R'_1$ or $R'_2$ is chosen from a cationic radical; or A3) diamino-N,N-dihydropyrazolone derivatives according to formula (III) below, addition salts thereof, solvates thereof, or solvates of the salts thereof:

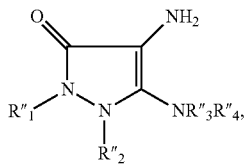

(III)

wherein:
$R''_3$ and $R''_4$, which may be identical or different, are chosen from:
a hydrogen atom;
a linear or branched $C_1$-$C_6$ alkyl radical optionally substituted with at least one radical chosen from a $OR''_5$ radical, a $NR''_6R''_7$ radical, a carboxyl radical, a sulfonic radical, a carboxamido $CONR''_6R''_7$ radical, a sulfonamido radical $SO_2NR''_6R''_7$, a heteroaryl, an aryl optionally substituted with at least one ($C_1$-$C_4$)alkyl, hydroxyl, $C_1$-$C_2$ alkoxy, amino, or (di)alkyl($C_1$-$C_2$)amino groups;

an aryl radical optionally substituted with at least one ($C_1$-$C_4$)alkyl, hydroxyl, $C_1$-$C_2$ alkoxy, amino, or (di)alkyl($C_1$-$C_2$)amino;

a 5- or 6-membered heteroaryl radical, optionally substituted with at least one radical chosen from ($C_1$-$C_4$)alkyl or ($C_1$-$C_2$)alkoxy; or $R''_3$ and $R''_4$ optionally form, together with the nitrogen atom to which they are attached, a 5- or 7-membered heterocycle, the carbon atoms of which may be replaced with an optionally substituted oxygen or nitrogen atom;

$R''_5$, $R''_6$, and $R''_7$, which may be identical or different, are chosen from:
a hydrogen atom;
a linear or branched $C_1$-$C_4$ alkyl radical optionally substituted with at least one radical chosen from hydroxyl, $C_1$-$C_2$ alkoxy, carboxamido $CONR''_8R''_9$, sulfonyl $SO_2R''_8$, aryl optionally substituted with a ($C_1$-$C_4$)alkyl, hydroxyl, $C_1$-$C_2$ alkoxy, amino, or (di)alkyl($C_1$-$C_2$)amino, aryl optionally substituted with a ($C_1$-$C_4$)alkyl, hydroxyl, $C_1$-$C_2$ alkoxy, amino or (di)alkyl($C_1$-$C_2$)amino; or $R''_6$ and $R''_7$, which may be identical or different, are optionally chosen from a carboxamido radical $CONR''_8R''_9$ or a sulfonyl radical $SO_2R''_8$;

$R''_8$ and $R''_9$, which may be identical or different, are chosen from a hydrogen atom, a linear or branched $C_1$-$C_4$ alkyl radical optionally substituted with at least one hydroxyl or $C_1$-$C_2$ alkoxy; and $R''_1$ and $R''_2$ form, together with the nitrogen atom(s) to which they are attached, a saturated or unsaturated 5- to 7-membered heterocycle optionally substituted with at least one radical chosen from halogen atoms and amino, (di)alkyl($C_1$-$C_4$)amino, hydroxyl, carboxyl, carboxamido and ($C_1$-$C_2$)alkoxy radicals, $C_1$-$C_4$ alkyl radicals optionally substituted with at least one hydroxyl, amino, (di)alkylamino, alkoxy, carboxyl, or sulfonyl radicals.

18. The composition according to claim 1, wherein the at least one 2-amino-5-ethylphenol coupler is present in a total amount ranging from about 0.0001% to about 20% by weight, relative to the total weight of the composition.

19. The composition according to claim 1, wherein the at least one 2-amino-5-ethylphenol coupler is present in a total amount ranging from about 0.005% to about 10% by weight, relative to the total weight of the composition.

20. The composition according to claim 1, wherein the at least one 2-amino-5-ethylphenol coupler is present in a total amount ranging from about 0.01% to about 6% by weight, relative to the total weight of the composition.

* * * * *